(12) United States Patent
Ahrens

(10) Patent No.: US 10,517,691 B2
(45) Date of Patent: Dec. 31, 2019

(54) DEVICE FOR PROVIDING A STERILE LIMITED SPACE FOR SURGERY

(71) Applicant: SURGITENT GmbH, Hamburg (DE)

(72) Inventor: Michael Ahrens, Neustadt i.H. (DE)

(73) Assignee: SURGITENT GMBH, Hamburg (DE)

(*) Notice: Subject to any disclaimer, the term of this patent is extended or adjusted under 35 U.S.C. 154(b) by 228 days.

(21) Appl. No.: 15/538,420

(22) PCT Filed: Dec. 23, 2014

(86) PCT No.: PCT/EP2014/079239
§ 371 (c)(1),
(2) Date: Jun. 21, 2017

(87) PCT Pub. No.: WO2016/102018
PCT Pub. Date: Jun. 30, 2016

(65) Prior Publication Data
US 2017/0340407 A1   Nov. 30, 2017

(51) Int. Cl.
*A61B 90/40* (2016.01)
*A61B 17/34* (2006.01)
(Continued)

(52) U.S. Cl.
CPC .......... *A61B 90/40* (2016.02); *A61B 17/3423* (2013.01); *A61B 17/3431* (2013.01);
(Continued)

(58) Field of Classification Search
CPC ... A61B 90/40; A61B 17/3423; A61M 1/0088
See application file for complete search history.

(56) References Cited

U.S. PATENT DOCUMENTS

| 2,741,410 A | 4/1956 | La Violette |
| 4,550,713 A | 11/1985 | Hyman |
(Continued)

FOREIGN PATENT DOCUMENTS

| EP | 0286525 | 10/1988 |
| EP | 0286525 | 12/1988 |
(Continued)

OTHER PUBLICATIONS

Wang Ying, Zhang Jing, Search Report: Notification of the First Office Action (PCT Application Entry Into the National Phase), Jul. 2, 2019, The National Patent Office PRC, CN-KnowHow Intellectual Property Agent Limited, Beijing, China 100080.
(Continued)

*Primary Examiner* — Andrew Yang
(74) *Attorney, Agent, or Firm* — Price Heneveld LLP

(57) ABSTRACT

A device for establishing and maintaining a sterile environment for conducting surgical procedures is disclosed. In particular, the tent-like device provides an interior space attachable to a patient's skin to allow surgical treatment of the patient. Several aspects of the invention are directed to devices to be used in connection with such a surgical procedure using the tent-like device. According to the invention, an isolation device for providing a sterile operation chamber above a skin region of a patient is provided, in particular for performing a surgical procedure, said isolation device comprising an inflatable bag coupled to a support frame, the support frame having a transport configuration and an operation configuration. In the transport configuration, the first inflatable bag is confined, such as to have compact dimensions. In the operation configuration, the first inflatable bag is extended, such as to form said sterile operation chamber.

5 Claims, 17 Drawing Sheets

(51) Int. Cl.
*A61B 42/50* (2016.01)
*A61B 50/13* (2016.01)
*A61B 50/15* (2016.01)
*A61B 50/10* (2016.01)
*A61B 50/20* (2016.01)
*A61L 2/18* (2006.01)
*A61F 13/00* (2006.01)

(52) U.S. Cl.
CPC .............. *A61B 42/50* (2016.02); *A61B 50/10* (2016.02); *A61B 50/13* (2016.02); *A61B 50/15* (2016.02); *A61B 50/20* (2016.02); *A61B 2050/105* (2016.02); *A61B 2050/21* (2016.02); *A61B 2217/005* (2013.01); *A61B 2217/007* (2013.01); *A61F 13/00085* (2013.01); *A61L 2/18* (2013.01)

(56) References Cited

U.S. PATENT DOCUMENTS

| | | | |
|---|---|---|---|
| 4,767,405 A * | 8/1988 | Lokken | A61M 25/02 128/DIG. 26 |
| 4,778,446 A | 10/1988 | Jensen | |
| 4,915,272 A | 4/1990 | Vlock | |
| 5,456,354 A | 10/1995 | Wood | |
| 5,758,660 A | 6/1998 | Oddvin | |
| 5,979,403 A | 11/1999 | Brogdon et al. | |
| 6,755,196 B2 * | 6/2004 | Musso | A61B 46/00 128/849 |
| 6,814,700 B1 | 11/2004 | Mueller et al. | |
| 7,037,254 B2 | 5/2006 | O'Connor et al. | |
| 2006/0021621 A1 | 2/2006 | Kriek | |
| 2007/0172396 A1 | 7/2007 | Neeper et al. | |
| 2008/0041399 A1 | 2/2008 | Kriek | |
| 2012/0042808 A1 | 2/2012 | Allen et al. | |
| 2014/0163326 A1 | 6/2014 | Forsell | |
| 2014/0242542 A1 | 8/2014 | Jubenville | |

FOREIGN PATENT DOCUMENTS

| | | |
|---|---|---|
| EP | 1092404 | 4/2001 |
| GB | 2401048 | 11/2004 |
| JP | S63-275348 A | 11/1988 |
| WO | 1986006272 | 11/1986 |
| WO | 9400090 | 1/1994 |
| WO | 03032819 | 4/2003 |
| WO | 2005053477 | 6/2005 |
| WO | 2005102185 | 11/2005 |
| WO | 2013138449 | 9/2013 |
| WO | 2014056640 | 4/2014 |

OTHER PUBLICATIONS

Violante, Karen, Search Report: Examination Report No. 1 for Standard Patent Application, Sep. 1, 2019, Australian Government IP Australia, www.ipaustralia.gov.au.

* cited by examiner

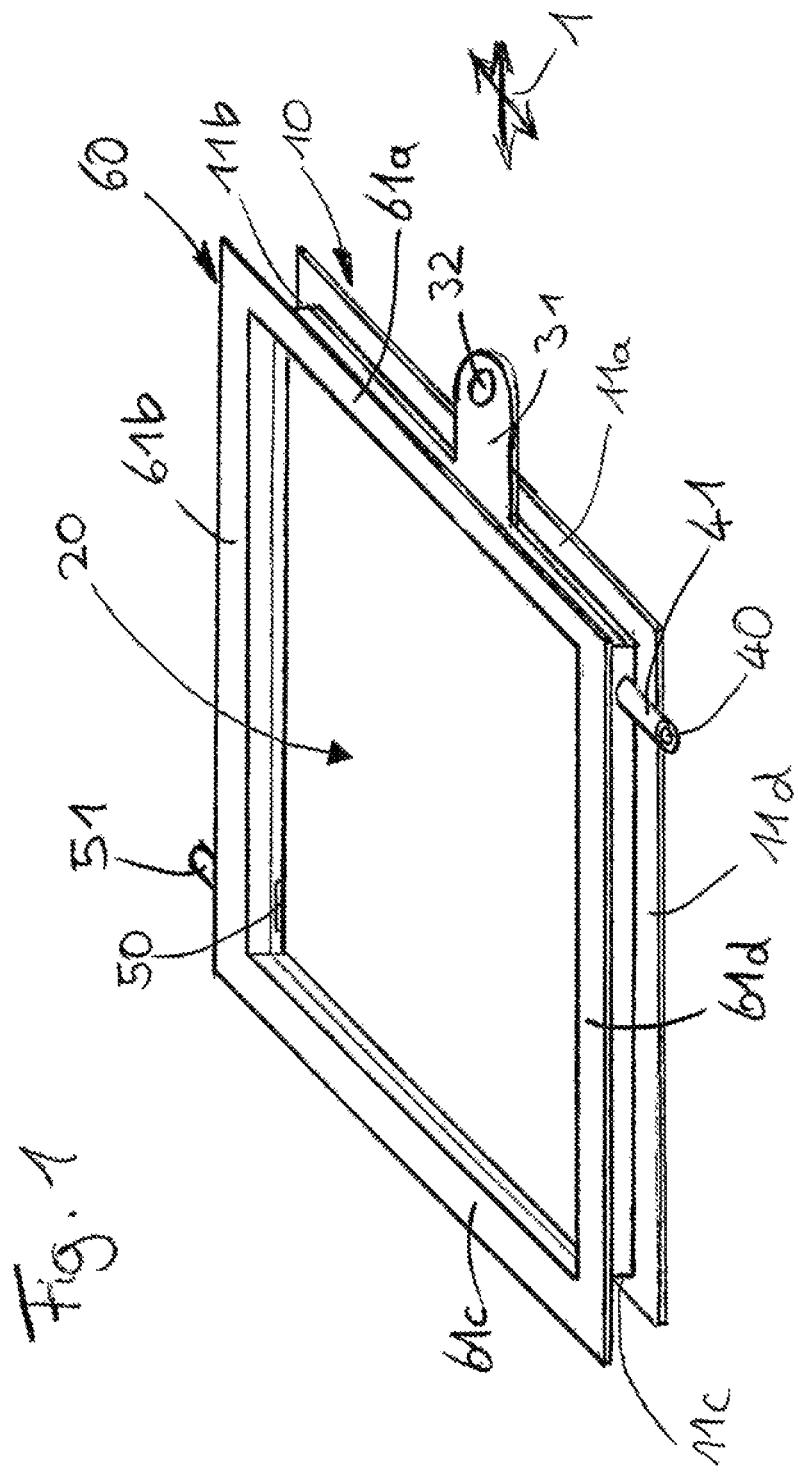

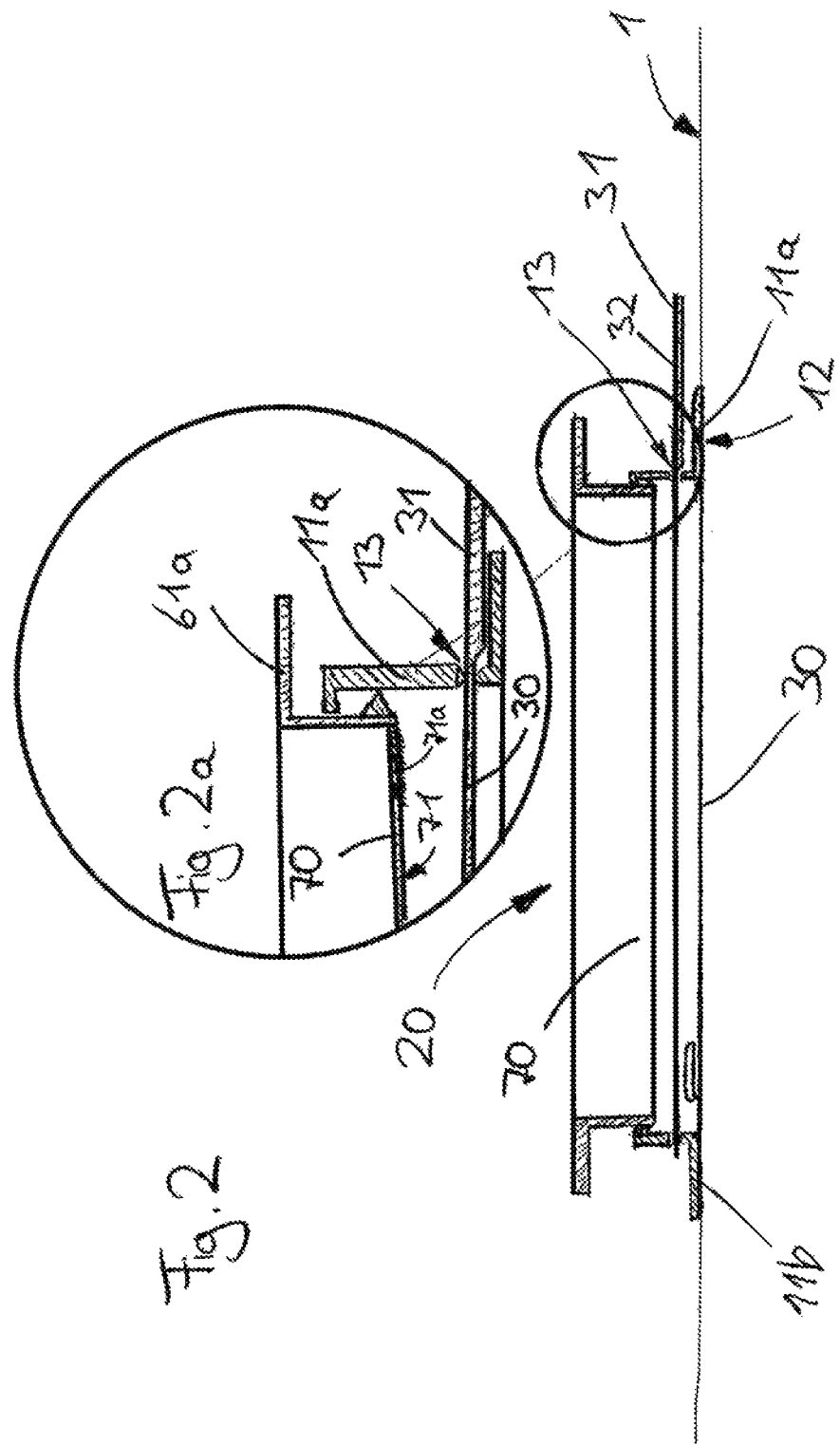

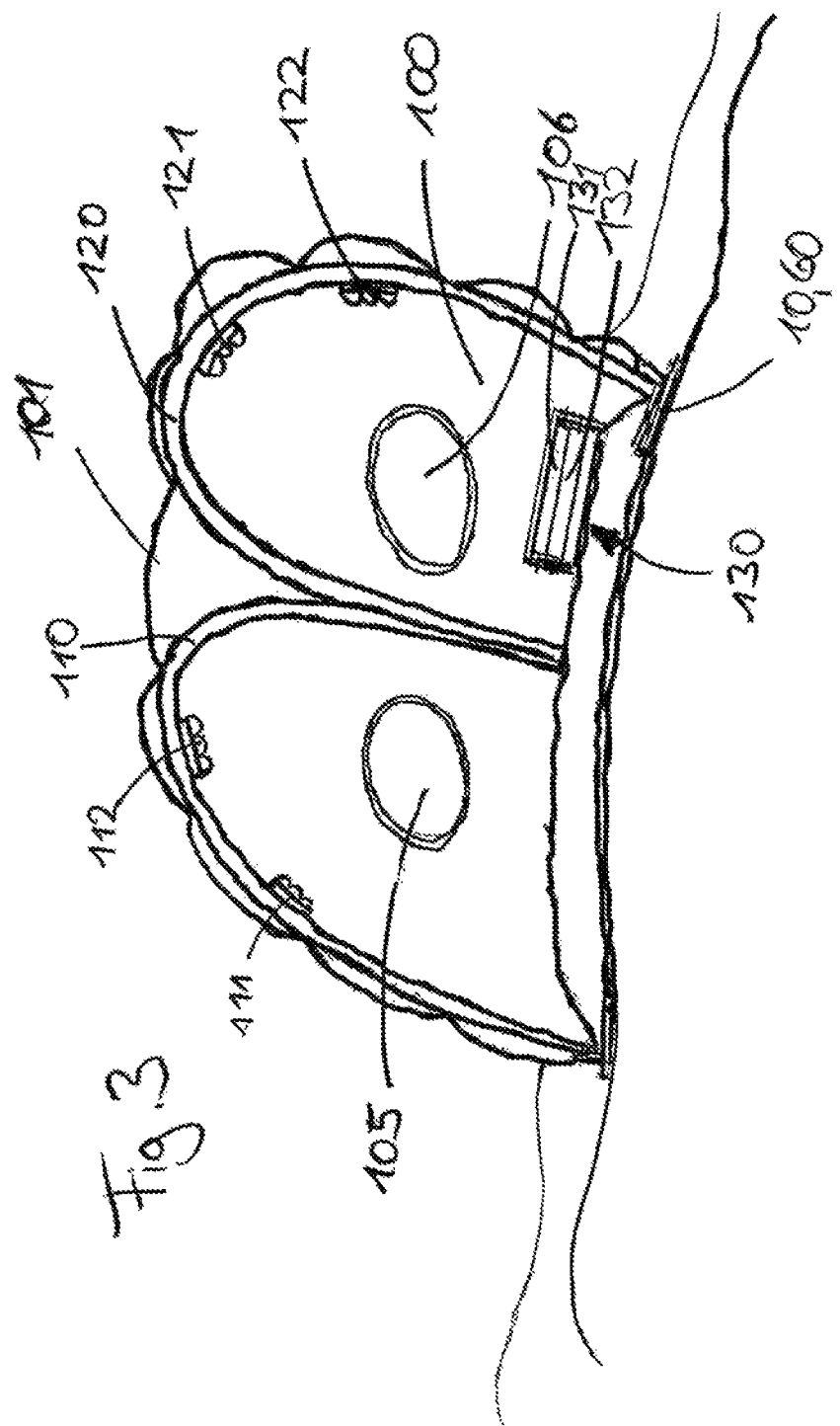

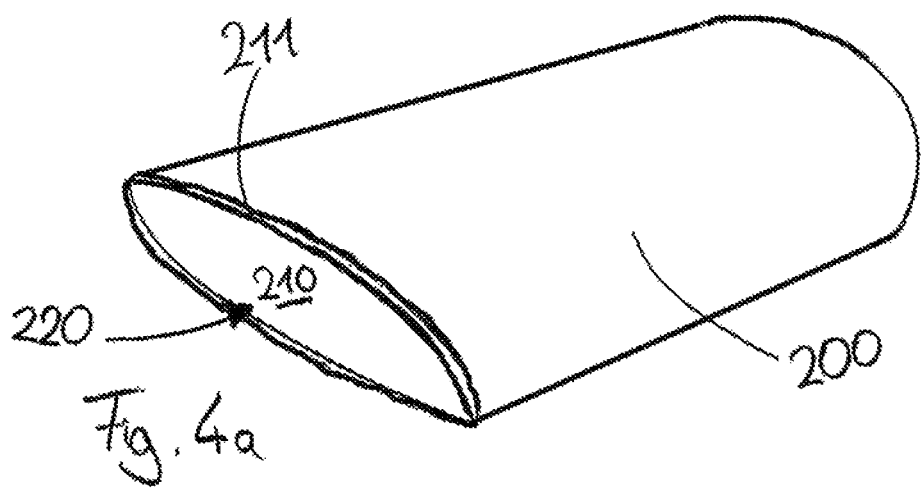
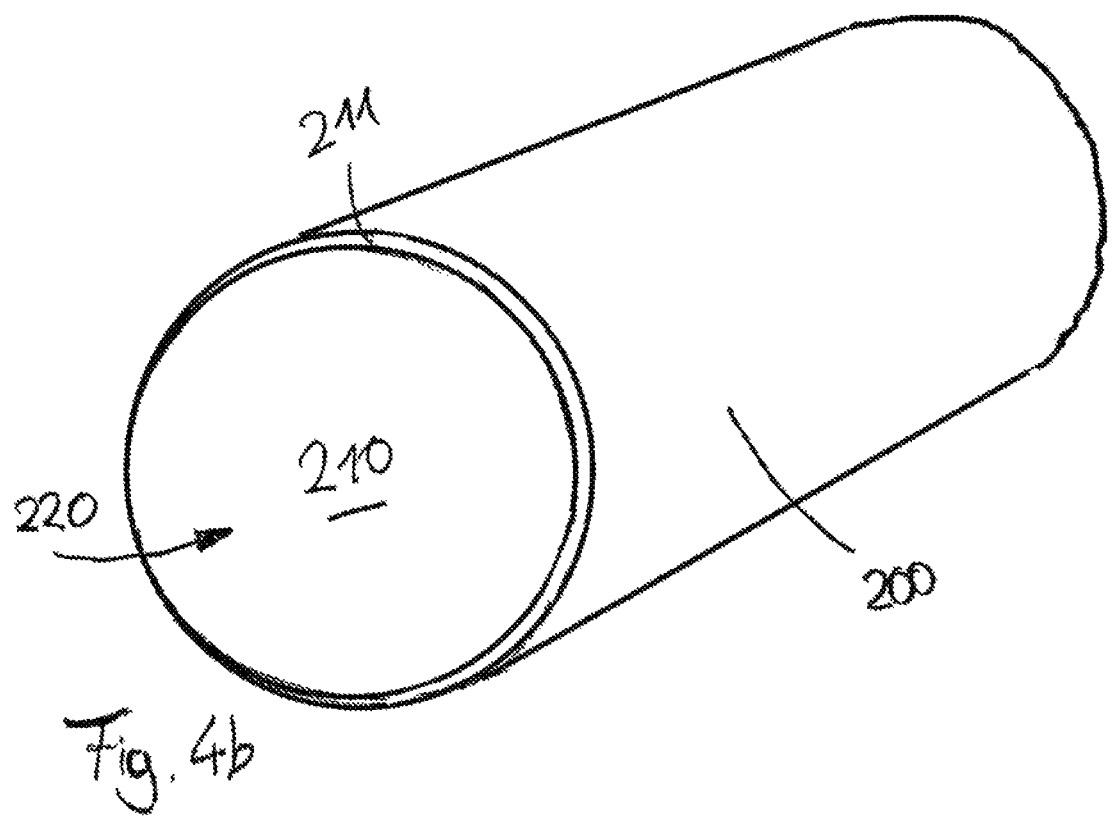

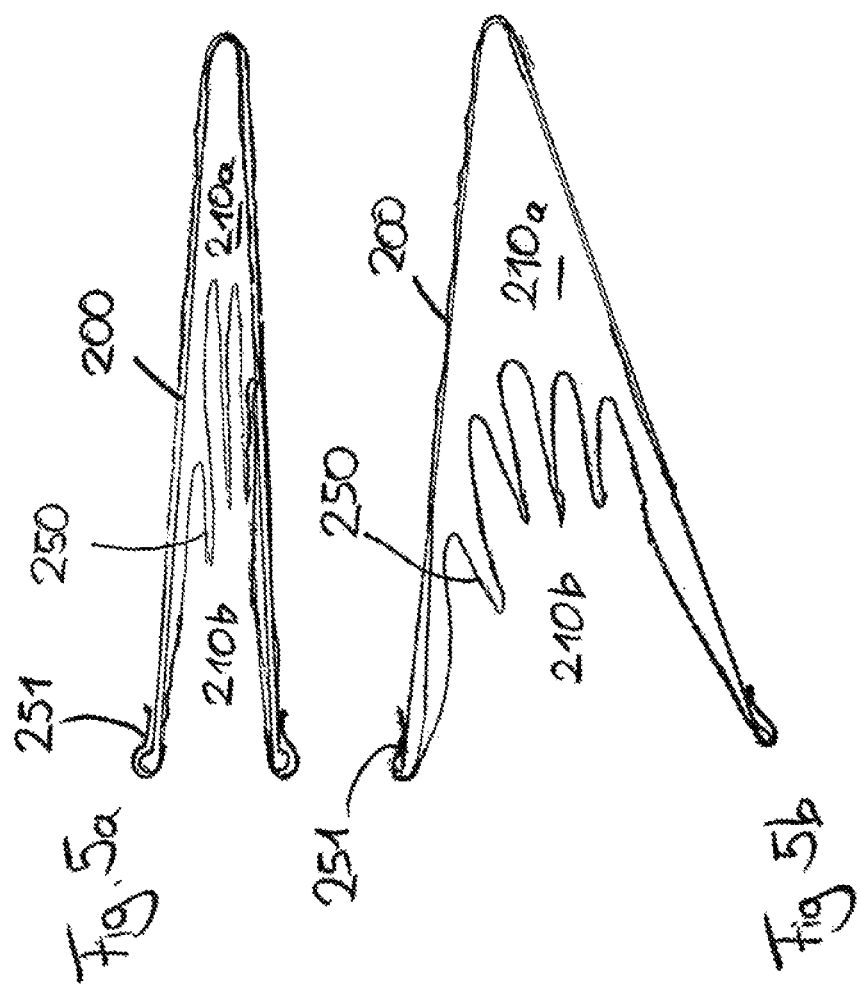

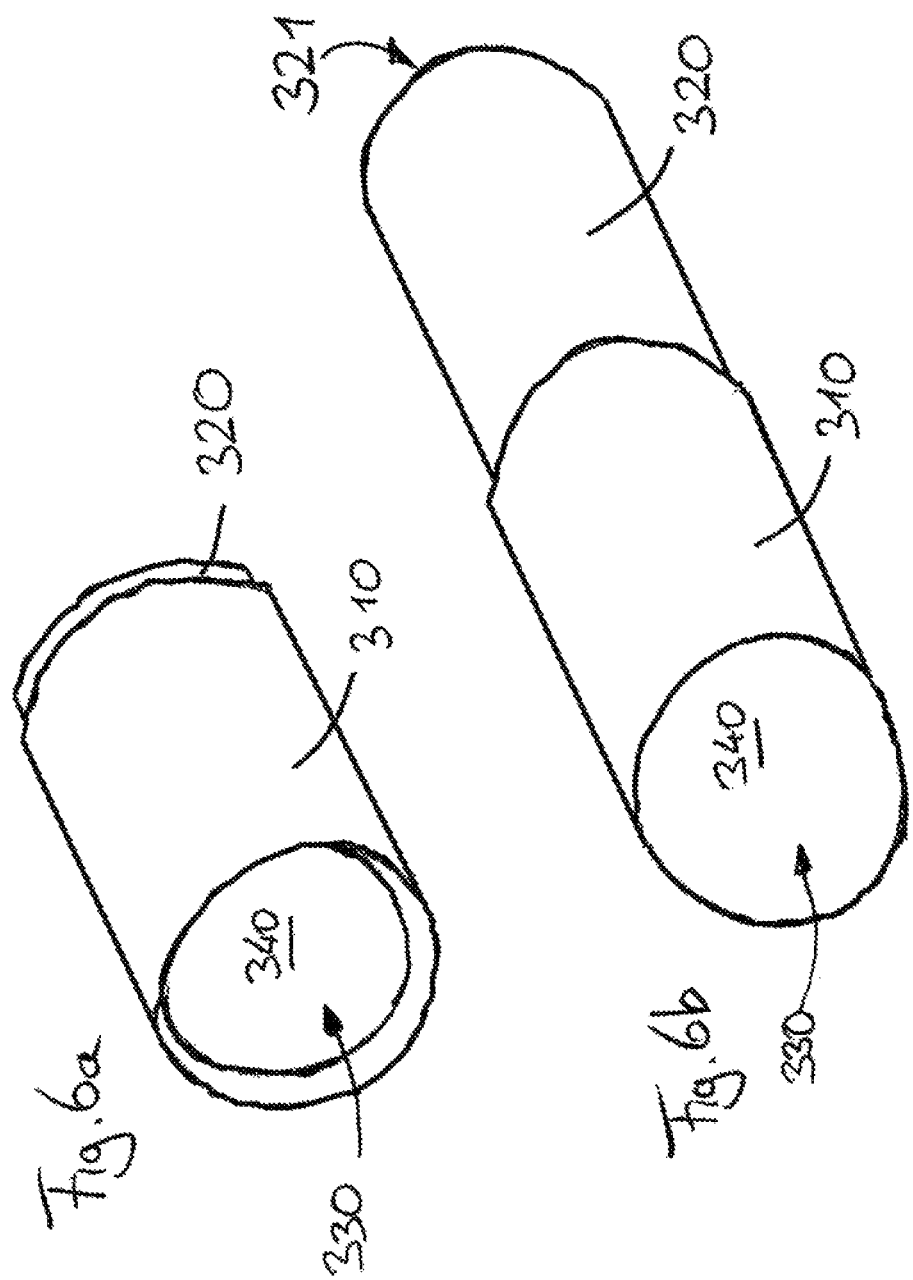

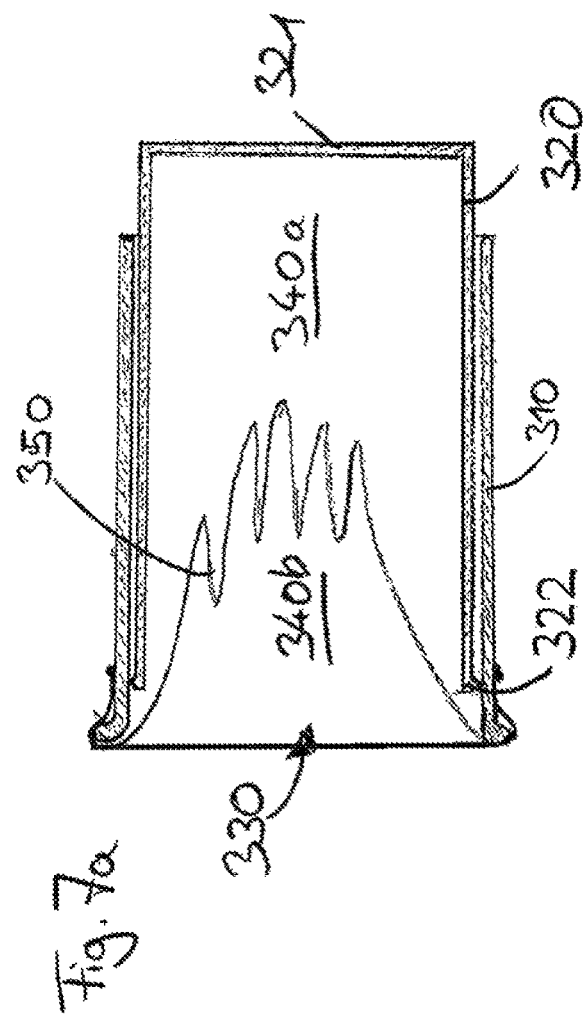
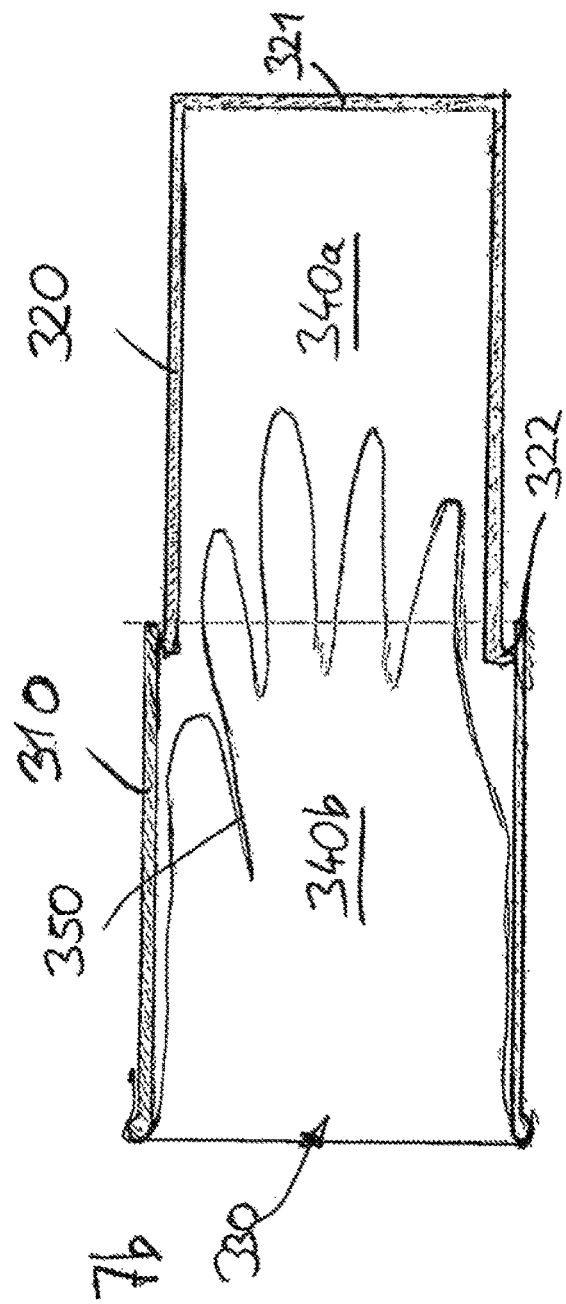
Fig. 7a
Fig. 7b

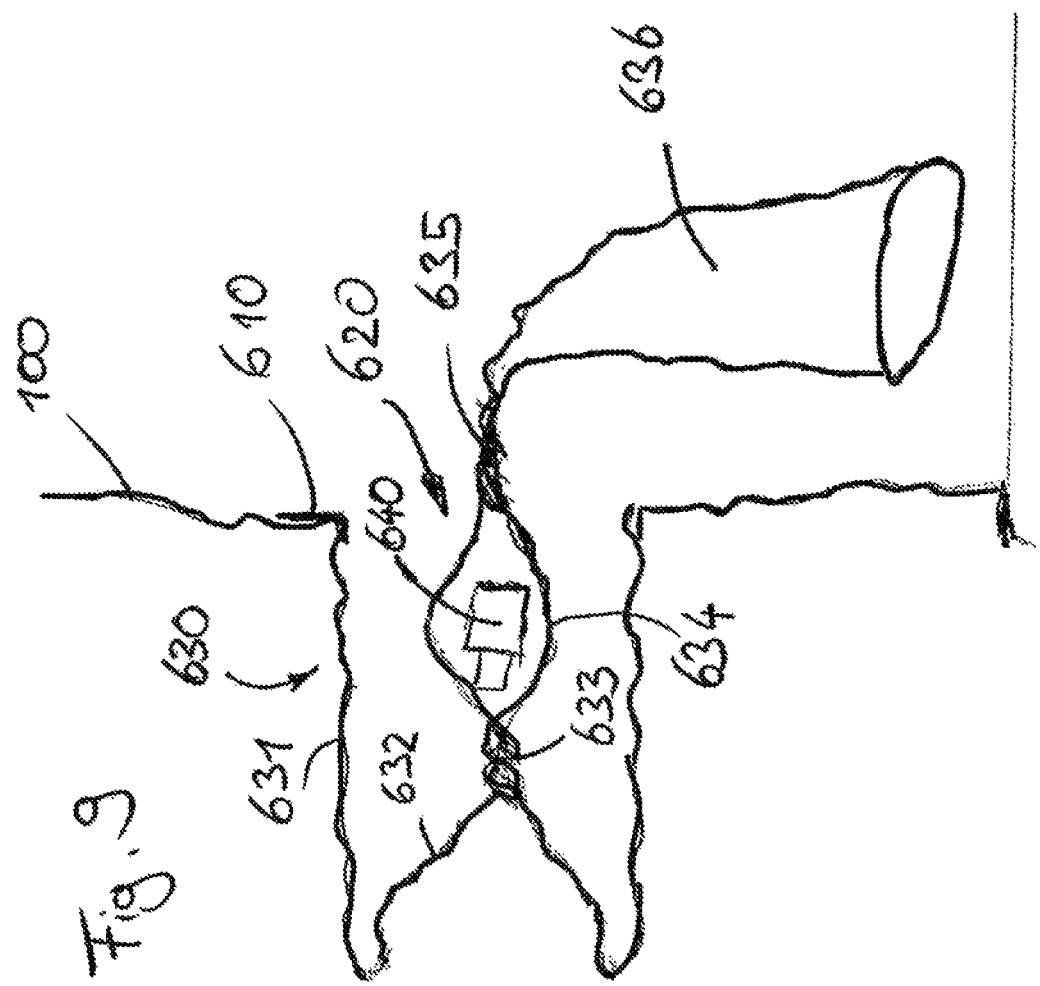

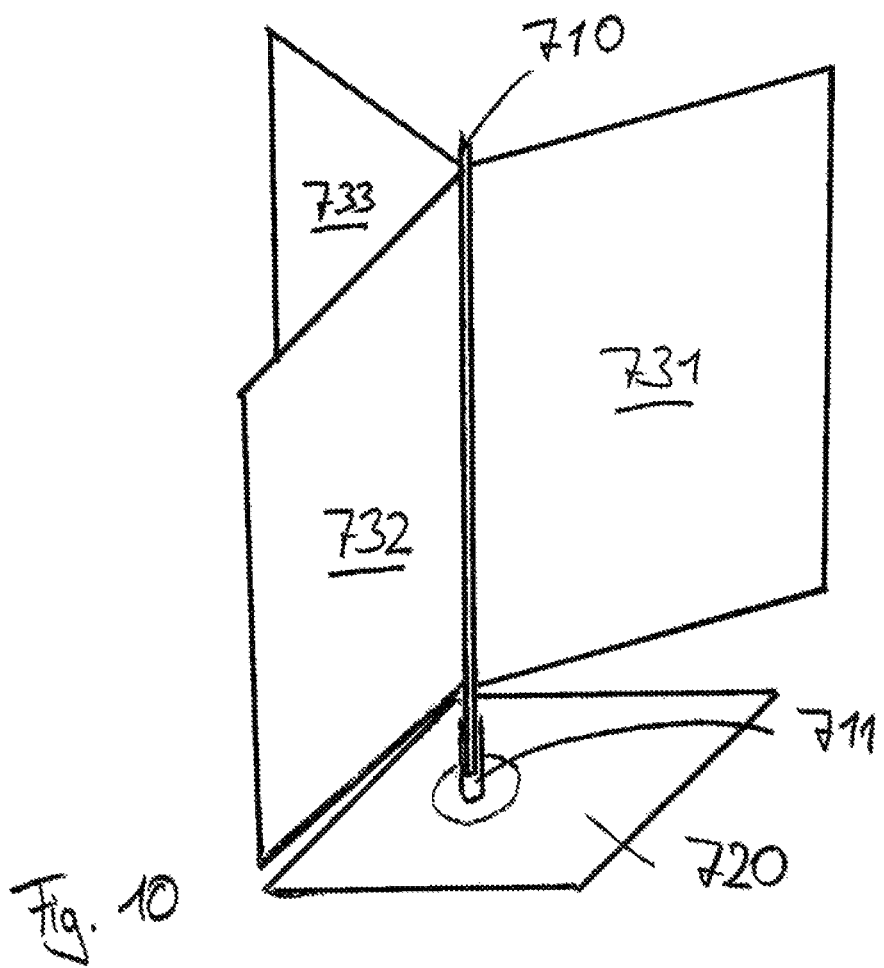

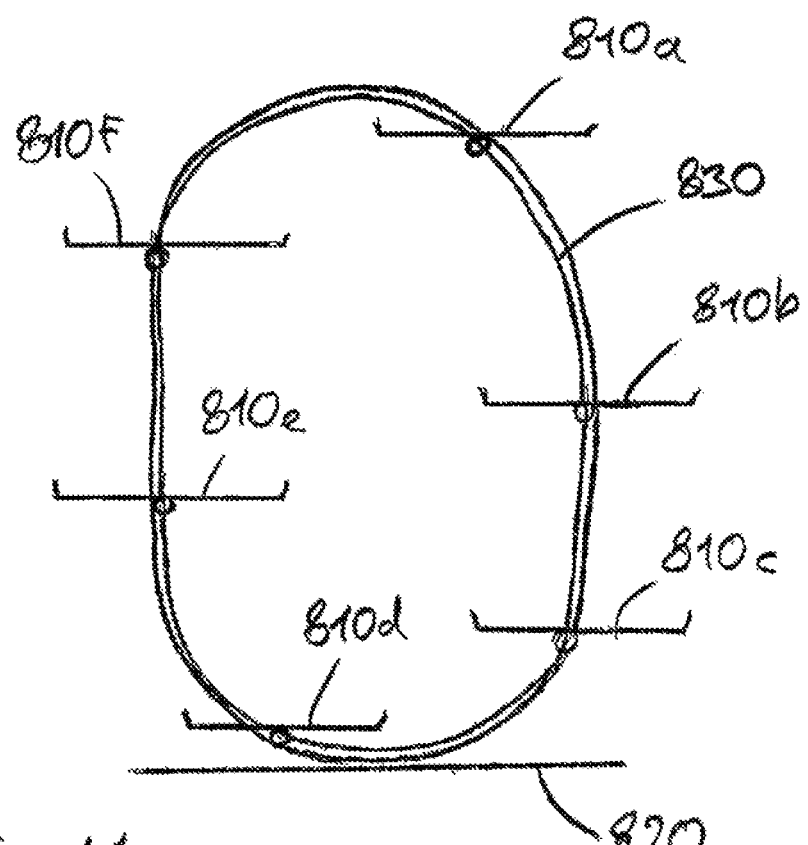

DEVICE FOR PROVIDING A STERILE LIMITED SPACE FOR SURGERY

CROSS-REFERENCE TO FOREIGN PRIORITY APPLICATION

The present application claims the benefit under 35 U.S.C. § 120 of PCT/EP2014/079239 filed Dec. 23, 2014, entitled "A Device for Providing A Sterile Limited Space for Surgery."

FIELD OF THE INVENTION

The invention relates to a device for establishing and maintaining a sterile environment for conducting surgical procedures. In particular, the tent-like device provides an interior space and is attachable to a patient's skin to allow surgical treatment of the patient. Several aspects of the invention are directed to devices to be used in connection with such a surgical procedure using the tent-like device.

BACKGROUND OF THE INVENTION

Today, in almost all applications of surgical invasive treatments requiring a major incision in the skin of a patient which needs to be maintained over a longer period of time, for example, for 30 minutes or for several hours, such treatments are undertaken in an operating room. Such an operating room provides a controlled atmosphere and environment as a whole and allows the patient to be positioned in a sterile space inside the operating room. Generally, this opens the possibility to conduct such a surgical invasive treatment without the risk of infection of the patient following migration of bacteria in the course of the operation. However, this must be considered a theoretical finding in view of the practical circumstances when conducting such a surgical procedure.

In practice, one major aspect for the success of such a surgical invasive operation with regard to being infectionless is the preparation of the patient and the preparation of the persons conducting the operation, such as the surgeon and assisting personnel. Major efforts requiring significant time are made to establish sterile surfaces of the patient, the surgeon, and the assisting personnel and any devices, such as instruments, handles of medical devices inside the operating room, and the like are employed to prevent any source of infection. However, in view of large medical devices, such as x-ray apparatuses, additional imaging devices, and further pneumatically or electrically driven apparatuses, such as the surgical illumination device and the like, a completely sterile preparatory work on all these devices and surfaces is a rather difficult task and thus in single cases no such complete disinfection and sterile environment is reached.

The costs for building and maintaining such an operating room and all devices inside said operation room and the costs for preparing and maintaining such operating room and any such devices in a sterile condition are high. Further, the preparatory work for a surgical treatment takes considerable time, thus not allowing a frequent processing of multiple surgical treatments in one operating room. This provides a significant drawback in particular with regard to surgical invasive treatments wherein such treatments do not take much time and it thus would be desirable to conduct multiple, short time treatments in one operating room, one after the other without significant preparatory work for disinfecting the room and the surfaces.

It is generally desirable to facilitate such invasive surgery treatment with regard to the preparatory work and to increase the safety against infections of the surgery's side in the course of such surgical treatments. Further, it is desirable to reduce the time and effort spent for such a surgical treatment and, in particular, the time spent for preparatory work for such surgical treatment to allow such invasive surgical treatments to be conducted in an environment at lower costs and in shorter time periods.

WO 1986/006272 A1 discloses an isolator for use in surgery. The isolator includes an inflatable bag of flexible material and a device for maintaining a positive pressure in the bag. The inflatable bag can be fixed to a patient and a surgeon can insert his hands into the inflatable bag to conduct a surgical invasive treatment inside said bag. Whereas such a bag having a positive pressure is considered to be safe against invasion of bacteria due to the pressure drop against the environment, the positive pressure inside said flexible bag is considered to bear on the risk of inducing embolism to the patient in the course of the surgical treatment by effecting local clotting or coagulation of the blood and pressing such clotted blood or the pressurized air directly into the body and the circular system of the patient. U.S. Pat. No. 7,037,254 B2 discloses a further device having an inflatable plastic dome to establish a controlled surgery environment by such inside pressurized atmosphere.

The use of such inflatable designs made of flexible sheet material has not shown to provide significant improvement with regard to preparatory work and conducting of surgical invasive treatment. As a first reason for this, the known devices require significant preparatory work on the patient to establish the sterile environment inside the inflatable bag. Further, the preparatory work is further complicated with regard to the planning of the treatment due to the fact that the surgeon is hindered from introducing additional instruments into the inflatable bag once the surgical treatment has started and is further hindered from removing tissue material or fluids out of the inflatable bag during the course of the surgical treatment. Thus, the approach of using such inflatable bags did not find acceptance in practice.

A further aspect considered as a significant drawback of such devices for establishing a local limited controlled atmosphere above a patient's skin for such a surgical treatment is the preparatory work for disinfecting the patient's skin. Such disinfection procedure often hinders a secure and rigid attachment of the inflatable bag to the patient's skin and thus bears on the risk of leakage as a result from the disinfection procedure of the patient's skin.

A still further drawback related to surgical treatments in general and specifically such surgical treatments using inflatable bags for establishing a limited sterile space is the preparatory work of the surgeon and assistant personal, in particular related to the gloves to be used by the surgeon and the personal. It is known that when putting such surgical gloves on the hands there is a significant risk of contaminating the exterior surface of the glove or damaging the glove due to the difficult handling of the gloves and the thin elastic material the gloves are made from. Further, it is known that taking off such gloves bears the significant risk of contamination to the user of the gloves from infectious substances attached to the exterior surface of the gloves.

In this regard, U.S. Pat. No. 2,741,410 discloses an apparatus for handling contaminated gloves wherein a person may insert his hand with the glove into a box to sealingly engage with the wrist of the person and a vacuum is applied to said box to release the glove from the hand of the person. By this, the taking off of such gloves may be facilitated.

However, the apparatus is bulky and requires significant technical means to allow taking off of such gloves. U.S. Pat. No. 4,915,272 discloses a further, more compact apparatus for donning and removing gloves by applying a vacuum to the exterior of the gloves. According to one embodiment, a device having a rigid perforated negative form of a hand with increased dimension is used to insert a hand wearing a surgical glove into said form and to apply a vacuum to take off such a glove. However, whereas this device provides function for taking off the gloves in an efficient procedure, it is rather impossible to use such a device for putting on gloves since a glove cannot be placed inside such a negative form without a hand being inserted into the glove or the form, which is not possible.

A further problem related to sterile limited spaces established on a patient's skin for conducting invasive surgical treatment, is how to provide or exchange surgical instruments and devices inside such limited space for conducting surgical treatments requiring a significant number of such instruments and devices. Generally, any process of introducing such instruments and devices into the limited space inside such an inflatable bag is considered to potentially induce contamination of the sterile atmosphere inside the bag and thus should be avoided. Further, the arrangement of a large number of instruments and devices inside such an inflatable bag is not possible due to the limited space and the range of motion of the surgeon for grasping such instruments.

It is a general object of the invention to provide an option for conducting invasive surgical treatments with less time spent for preparatory work and less risk of infection for the patient. It is a specific object of the invention to provide a device wherein the planning and the logistics of such a surgical treatment can be simplified and is less sensitive to unforeseen events in the course of a surgical treatment.

SUMMARY OF THE INVENTION

According to the invention, these and other objects are solved by a device for producing and maintaining a sterile surface on a patient's skin comprising: a first frame having first frame elements encompassing a first inner operation opening allowing access through said first frame from a top side of the first frame to a bottom side of the first frame, said first frame elements having a downward first adhesion surface including an adhesive material adapted to adhere said first adhesion surface to the patient's skin. A first foil is attached to the first frame and extends across said inner operation opening. A fluid channel is provided in said first frame, said fluid channel being in fluid communication with a connector for injecting fluid into said fluid channel, wherein said fluid channel opens into a space between the bottom side of the first frame and the first foil to allow flooding of a space defined between the first foil and the patient's skin if the first frame is attached to said patient's skin.

According to this aspect of the invention, a specific device is provided which can be employed and used for producing a sterile surface on a patient's skin. The device comprises a first frame which can be composed of one single frame element which is bent to define a closed structure circumscribing an inner operation opening. The first frame can in the same way be composed of multiple components connected to each other to define such a closed structure and to circumscribe said first inner operation opening. The inner operation opening defines the area on the skin of the patient which is accessible for the surgeon to conduct the surgical operation. The first frame elements have a downward adhesion surface which may comprise an adhesive tape or any other adhesive material which is capable of establishing a safe and tight adhesive and sealed contact to the patient's skin. It is to be understood that this adhesive contact must be releasable to allow removal of the first frame after the end of the surgical operation. A first foil extends across said inner operation opening in such a way that said first foil completely covers the first opening. The first foil is attached to the first frame in a sealing engagement. Preferably, the first foil is flexible and further preferable the first foil is semi-transparent or transparent. Generally, the first foil has a lower surface facing to the skin in use of the device, which is adapted to not adhesively attach to the skin such that a disinfecting agent can be inserted into the space between the skin and the first foil.

In use of the device according to the invention, the first frame is attached to the patient's skin in an area circumscribing that skin region wherein the incision for the surgical operation is to be made, such that this skin region lies in the first inner operation opening and is covered by the first foil. A fluid channel is included in said first frame allowing access from outside of the first frame to the first inner operation opening. A connector is provided allowing to insert a fluid material, in particular a liquid disinfecting or sterilizing agent through said fluid channel. The fluid channel opens into a level which is lying between the downward first adhesion surface and the first foil attached to the first frame. By this, a fluid can be inserted through said fluid channel into a space which is defined by the first foil, the first frame and the skin of the patient if the first frame is attached to said skin with the downward first adhesion surface. In use of the device, a disinfecting or sterilizing agent is injected via said fluid channel into this space such that the whole space between the first foil and the skin of the patient encompassed by the first frame is flooded with the sterilizing and disinfecting agent. This flooded condition may be maintained for a certain period of time to make sure that the effect of sterilizing the skin surface and the downward surface of the first foil is fully accomplished. Thereafter, the fluid is withdrawn which can be accomplished by applying a suction force to the fluid channel and thus withdrawing the fluid out of the space between the first foil and the skin. The process may be repeated once, twice or more, such that a safe sterile condition is produced. Hereafter, the fluid channel may be used to ventilate sterile filtered dry air through the space between the first foil and the skin to facilitate a fast drying of the space. Hereafter, the fluid channel may be closed by a plug or the like, being inserted into the connector and the surgical operation can be started.

In a simplified setup, the surgeon may hereafter cut out the first foil or the first foil may be designed in such a way as to attach to the skin after the sterilizing fluid has been removed such that the surgeon may use the first foil as a protective foil attached to the skin and cut the first foil like the skin in the course of the operation.

According to a preferred embodiment, the first foil comprises a removal extension for removing the first foil, the device further comprising: a second frame having second frame elements encompassing a second inner operation opening; a second foil, attached to the second frame and extending across said second inner operation opening; said second frame having an outer dimension such that the second frame fits into the first frame; said second frame elements having a downward second adhesion surface including an adhesive material adapted to adhere said second adhesion surface to the patient's skin upon removal of the first foil. According to this preferred embodiment a second foil is provided and the first foil is adapted to be removed by simple means like a grasping section, a handle or the like. The second foil is attached to a second frame and this second frame circumscribes a second inner operation opening. The second inner operation opening is almost completely congruent to the first inner operation opening such that the second frame fits into the first frame. The second frame is movable in relation to the first frame and in a first relative position to the first frame the second frame, the first frame, the first foil and the second foil sealingly enclose an inner space and said inner space is sterile. After sterilizing the skin of the patient via the flooding operation as described beforehand, the first foil can thus be removed and by this said inner space opens to the skin. Due to the sterile nature of said inner space the sterile condition of the skin is maintained by this. The second frame can then be moved in relation to the first frame and hereby the second foil is brought into contact with the skin. The second frame has a downward second adhesion surface which can be adhered to the patient's skin or can alternatively be adhered to the first frame. By this, the second frame and the second foil can be fixed in relation to the skin. Preferably, the second foil has a downward adhering surface for adhering to the skin and is configured to be a protective foil as commonly used in surgical operation to protect the skin around an incision of a surgical operation. Using this preferred embodiment thus allows to safely and conveniently use and apply such a protective foil in the course of the preparatory work of sterilizing the patient's skin and preparing it for the surgical operation.

According to a further preferred embodiment, the second foil has a bottom surface facing towards a bottom side, wherein said bottom surface is coated with a first adhesive material adapted to attach said second foil, preferably a center region of said second foil, to the skin of the patient, wherein preferably an edge region of said second foil is reinforced and/or is coated with a second adhesive material having stronger adhesive properties than said first adhesive material. According to this preferred embodiment, the second foil acts and functions as a protective foil to the skin of the patient in the region of the incision of the surgical operation. Further, the second foil establishes a safe sealing contact in an edge region close to the second frame preventing migration of any gaseous or liquid fluid or the like from outside the frame into the operation site and the incision region. Preferably, the adhesive material is applied in a pattern in the edge region which is different from the pattern in which it is applied in the central region of the second foil. Alternatively the adhesive material applied in the edge region of the second foil may be a different adhesive material than the adhesive material applied in the central region of the second foil.

According to a further preferred embodiment, a second fluid channel is provided in said first frame, said second fluid channel being in fluid communication with a second connector for removing fluid out of said second fluid channel, wherein said second fluid channel opens into said space between the bottom side of the first frame and the first foil to allow flooding of said space defined between the first foil and the patient's skin if the first frame is attached to said patient's skin. According to this embodiment, a second fluid channel is provided in said first frame and thus the insertion and the removal of the sterilizing agent is simplified in that the fluid may either be inserted via two channels, for example at opposed sides of the frame and thereafter withdrawn via said two channels or in an alternative procedure the agent may be inserted via the first fluid channel and may be withdrawn through the second channel. According to this embodiment, the connector provided for the first fluid channel and the connector provided for the second fluid channel might be identical but in specific applications, wherein the first channel serves to insert the sterilizing agent and the second channel serves to withdraw the sterilizing agent. The connectors may be different to prevent misuse of the connectors and the fluid channels. It is generally to be understood that both the first and the second fluid channel might include a check valve closing the fluid channel against a specific flow direction and might further include a valve which is pushed open by inserting a cannula, hollow needle or the like and which is closing the fluid channel upon removal of such cannula or needle. This will safely prevent migration of any fluids or bacteria through the fluid channel into the surgical site. In particular, this allows effective drying via continuous venting of the space and the skin and foil surfaces with dry air or the like.

According to a further preferred embodiment, a first fluid channel opens into said space on a first side of the frame and said second fluid channel opens into said space on a second side of the frame, which is opposite to said first side. According to this preferred embodiment, in both optional uses, i.e. insertion of the sterilizing agent via both fluid channels and withdrawing of said agent via both channels or alternatively insertion of the sterilizing agent via one fluid channel and withdrawing of the agent via the second channel, this can be conducted in such a way that complete coverage of the skin under the first inner operation opening is ensured by a specific opposite arrangement of the fluid channels.

According to a still further preferred embodiment, the first foil or said second foil is attached to a collapsible frame, wherein said collapsible frame in a first, upright condition defines side walls of a space having a cross section generally corresponding to said first or second inner opening, respectively, and wherein said collapsible frame can be collapsed to a second condition, wherein said collapsible frame is lying flat on said first or second foil, respectively, and protects an edge region of said foil against mechanical impact. According to this embodiment, a collapsible frame is provided, wherein said collapsible frame can be part of the first frame or part of the second frame or the first frame or the second frame can even be constituted by said collapsible frame. The collapsible frame in a first condition defines a space versus the skin and can be collapsed down to a second condition, wherein the collapsible frame lies flat on the skin or on said first or second foil in the edge region of the inner operation opening. By this, this edge region is sealed as a first function and is protected against incisions as a second function of the collapsible frame. It is to be understood that the collapsible frame preferably collapses in such a way that a sterile surface of the frame faces towards the operation site both in the first and the second condition such that no adverse effects occur in the course of the collapsing of this collapsible frame.

According to a further aspect of the invention, an assisting device for donning and removing a surgical glove is provided, said assisting device comprising: at least one fluid-tight wall arrangement, encompassing an inner space having a volume of such a size that at least a palm portion and finger portions of said surgical glove can be arranged in said space; an opening adapted to sealingly engage a cuff portion of said surgical glove if said palm portion and said finger portions are arranged in said space; characterized in that said fluid tight wall arrangement is adapted to be transformed from a first configuration into a second configuration and vice versa, wherein in said first configuration said inner space has a first inner volume; and in said second configuration, said inner space has a second inner volume, wherein the first volume is smaller than the second volume.

According to this aspect of the invention, a functional and simplified device is provided which allows a surgeon or any personal involved in a surgical operation a facilitated taking on and taking off of a surgical glove. The device comprises a fluid-tight wall which defines an inner space in a sealing arrangement. Said inner wall can be comprised from one single flexible wall element or by two or more wall elements connected with each other to circumscribe and seal said inner space. The inner space defined by said wall is dimensioned such that a hand can be taken up by said inner space and some clearance is provided between the hand and the wall if the hand is inserted into the inner space. An opening is provided at said wall allowing access to the inner space and said opening has a dimension such that a hand can conveniently reach through said opening into said inner space. The opening is adapted to sealingly engage a cuff portion of a surgical glove. This can be accomplished in a simplified way in that the cuff portion is put over an edge region of the wall circumscribing said opening by a sort of reverse drawing or the like. In other embodiments, the cuff portion of the glove may be clamped between an edge region of the wall close to the opening and an inner ring inserted into the cuff portion of the glove to provide such sealing engagement. By sealingly engage a glove in such a way to the opening a sealed space between the glove and the wall is established inside said inner space.

According to the invention, the fluid-tight wall can be transformed from a first configuration into a second configuration and vice versa. This transformation can be conducted by elastic deformation of the wall or by a relative movement of two wall elements versus each other or the like. Generally, the volume inside the fluid-tight wall is different in the first configuration versus the second configuration, such that the volume inside the fluid-tight wall is larger in the second configuration than in the first configuration. By this a specific effect occurs in that the sealed space between the fluid-tight wall and the glove is increased when transforming the fluid-tight wall from the first configuration to the second configuration and by this an extension force is applied to the glove by a vacuum applied to the outer surface of the glove facing towards the fluid-tight wall. By this, the glove is extended homogeneously and thus a surgeon or an assistant personal may easily slide his or her hand into the surgical glove to take off the glove. In the same way, a person wearing a surgical glove may insert his or her hand into the inner space, establish a sealing engagement in the cuff region of the glove/the hand and thereafter transform the fluid-tight wall from the first configuration into the second configuration to apply a vacuum to the outer surface of the glove. By this, the glove will be extended and will be lifted from the skin of the hand and at the same time will be held back inside the inner space if the person withdraws his/her hand out of the inner space thereafter. By this, the person may easily take off the surgical glove using the device according to the invention.

According to a first preferred embodiment, said wall arrangement comprises at least one flexible wall section, and wherein in said first configuration said flexible wall section has a first shape, thus defining said first inner volume; and in said second configuration said flexible wall section has a second shape, thus defining said second inner volume. According to this embodiment, the first and second configuration is accomplished by transforming the fluid-tight wall by a flexing motion and thus a reversible, elastic deformation of the fluid-tight wall is conducted to transform the fluid-tight wall from the first configuration into the second configuration and vice versa. According to this embodiment, the fluid-tight wall might have a flat elliptic cross-section in the first configuration and may be transformed into the second configuration having a cylindrical cross-section and thus an increased inner volume wherein one front face of said elliptical/cylindrical tube may be sealed by a flexible foil and the other front face may provide the opening for inserting the glove and the hand.

Still further, it is preferred that said flexible wall section is biased into said first shape, or said flexible wall section is biased into said second shape. According to this embodiment, the fluid-tight wall has a preferred configuration, either the first or the second configuration and thus is configured in said preferred configuration if no outer force is applied to the fluid-tight wall and can be transformed into the other configuration by applying such a force.

According to a further preferred embodiment, the assisting device is further improved by a second flexible wall section, wherein said second flexible wall section is coupled to said first flexible wall section along two opposed edges of said first and second flexible wall sections, wherein in said first configuration the first and second flexible wall sections form a flat pocket-like geometry with the first inner space being inside the pocket and in said second configuration said first and second wall section are bent outward to both form outer convex surfaces. According to this preferred embodiment, the fluid-tight wall is defined by two wall sections lying parallel to each other and having identical or almost identical dimension such as to form a pocket-like arrangement. In such a configuration, the two wall sections are connected at the opposed side edges to each other such as to allow a relative movement in the form of a hinge-like connection in these side edge regions, in particular, the two flexible wall sections may be connected by an integral hinge at the side edges. The front edges of the wall sections may define the edges around the opening into the inner space. The rear edges may be connected by an integral hinge in the same way as the side edges or may be sealed against each other by a flexible foil or the like connected to the rear edges of the wall sections such as to allow the rear edges to separate from each other into the second configuration. Such a pocket-like design of the assisting device thus provides a first, flat configuration with a small or zero inner volume and may easily be transformed into the second configuration by applying a pressure force onto the two side edges forcing the two wall sections apart and thus transforming the assisting device into a sort of elliptical or cylindrical cross-sectional geometry with a significantly increased inner volume. It is to be understood that instead of the fluid-tight wall comprising two such wall sections in further improved embodiments 3 or 4 such wall sections may be provided which are sealingly connected to each other via integral hinges or the like to provide the same functionality.

According to a further, alternative preferred embodiment, the assisting device is further improved in such a way that said fluid-tight wall arrangement comprises a first tube segment and a second tube segment, said second tube segment being slidable attached to a first ring segment so as to form a telescope-like arrangement, wherein said second tube segment can be slid into a fluid-tight sealing engagement towards an outer surface of said first tube segment; wherein the second ring segment can be slid onto said first ring segment in an axial direction from said first configuration into said second configuration, and in said first configuration the total length in the axial direction of the fluid tight wall arrangement comprised of said first and second ring segment is shorter than in said second configuration.

According to this preferred embodiment, the fluid-tight wall arrangement comprises two wall segments which are shaped as a tube wherein the second tube segment has an inner dimension adapted to conform to an outer dimension of said first tube segment, such that the second tube segment can slide on the outer surface of the inner tube segment. This sliding movement shall be a sealing sliding movement such that the inner space defined by the first and the second tube segment is always sealed against the environment even such that no fluid may flow through the contact region between the first and the second tube segment. It is to be understood that the invention may comprise a further third tube segment or even further additional tube segments wherein such third tube segment may be adapted to sealingly slide on the outer surface of the first tube segment or on the outer surface of said second tube segment. The first and second tube segment and potentially further tube segments such define a telescope-like arrangement allowing to arrange the tube segments in a first, short configuration wherein the first and the second tube segment overlap each other over a significant length and a second configuration having an elongated dimension wherein the overlap of the first and the second tube segment is significantly less than in the first configuration. By such a sliding movement the fluid-tight wall arrangement composed of the first and second and optionally further tube segments can easily be transformed from a first configuration into a second configuration wherein the inner volume is significantly increased by such sliding movement of the tube segments versus each other. In this preferred embodiment, one front end of a tube segment may serve as the opening to insert the glove and the hand into the inner space inside the tube segments and the other, rear end of the other tube segment may be sealed wherein such sealing shall not be flexible but a rather stiff sealing wall may be provided such that one of the two tube segments may have a cup-like configuration with the bottom of the cup forming the sealing rear end wall.

According to a further preferred embodiment, said fluid-tight wall arrangement comprises an elastic tube segment which can be elastically deformed from an elliptic cross-sectional shape in said first configuration to a circular cross-sectional shape in said second configuration.

According to a still further preferred embodiment, a fluid-tight seal is provided for providing said sealing engagement of said opening and said cuff portion, the fluid tight seal comprising a strap having an outer ring, an inner ring and at least one snap ring; wherein the at least one snap ring is adapted to secure the cuff portion of said surgical glove between an inner surface of the outer ring and an outer surface of the inner ring, said outer ring having an outer surface which can be partially inserted into said opening to sealingly engage said opening.

According to this preferred embodiment, a specific and convenient use is provided for the fluid-tight seal of the glove versus the opening in the cuff portion of the glove. This convenient sealing engagement is established by two rings wherein one of the two rings is an outer ring and arranged on the outside surface of the glove and the other ring is an inner ring arranged on the inner side of the glove and inside the outer ring. Thus, the outer surface of the inner ring is dimensioned such as to engage the inner surface of the outer ring and it is to be understood that a slight clearance might be present but a slight overlap may be possible, too with regard to the dimension of the outer surface of the inner ring and the inner surface of the outer ring as long as at least one of the two rings can be elastically deformed. Further, a snap ring is provided and this snap ring is adapted to apply a radially outwards directed force onto the inner ring to press said inner ring against said outer ring. By this, a glove can be safely and sealingly engaged between the inner and the outer ring. Further, the arrangement of the inner and outer ring with the glove clamped between the two rings can easily be sealingly engaged to the opening and thus, the use of the assisting device is further facilitated and made more convenient for a surgeon or assistant personal. Preferably, the outer ring may comprise one or two circumferential lamellae to sealingly engage an inner edge region of the fluid-tight wall close to the opening to establish such sealing engagement to the fluid-tight wall.

According to a still further preferred embodiment, said inner space comprises a first region adjacent to the opening and adapted to accommodate the palm portion of the surgical glove and a second region adjacent to the first region and adapted to accommodate the finger portions of the surgical glove, wherein in said first region the wall arrangement restricts the elastic stretching of the glove in the second configuration such that the palm region is stretched to an extent of less than 150%, preferably less than 125%, wherein said elastic stretching is restricted by a contact of an inner surface of said wall arrangement to said surgical glove in said first region. The inventor has found that some embodiments of surgical gloves show a significant extension in the palm region when applying an internal pressure into the glove or applying an external vacuum to the glove and this extension in the palm region is significantly higher than the extension in the finger region of the glove. The reason for this behavior can be found in the higher resistance and mechanical stability against deformation in the finger region than in the palm region of the glove. However, this behavior was found to be unfavorable when using such gloves in connection with the assisting device according to the invention, since a person may easily access the palm region of the glove, but may have problems when putting his fingers into the finger regions of the glove or removing his fingers out of the finger regions of the glove. Thus, according to this embodiment, the elastic deformation, this means the extension of the glove in the palm portion, is limited by the wall arrangement to a certain extent. This can be easily accomplished in that the palm portion of the glove abuts the inner surface of the wall arrangement when having reached a certain degree of extension. Hereafter, the palm portion of the glove is hindered from being further stretched or extended and thus the vacuum being applied to the glove when the sealing wall arrangement is further transformed into the second configuration will only apply an extension force to the finger portions of the glove. By this, a significant extension of the finger portions can be reached such that in an ideal setup both the palm portion and the finger portion are extended by a similar ratio and thus a user may conveniently insert or withdraw his/her hand into the glove or out of the glove in the such extended configuration.

It is to be understood that the assisting device according to the invention has a major advantage over prior art devices in that no external vacuum source like a vacuum pump or the like is required to use the device. Thus, the assisting device according the invention can be used in a closed environment and does not require any input of energy or the like to help a person in taking on or off surgical gloves. In particular, the assisting device can be used inside an inflatable bag arranged above a surgical site on a patient's skin and is completely independent from any pressure or vacuum condition inside such inflatable bag. It is further to be understood that the assisting device according to the invention may be a simplified disposable device equipped with one glove and can as such a device be provided inside a pre-packed package of such an inflatable bag to simply allow a surgeon to take off a glove provided inside the assisting device without the need for any help by an assisting personal or the like.

According to a further aspect of the invention, an isolation device for providing a sterile operation chamber above a skin region of a patient is provided, in particular for performing a surgical procedure, said isolation device comprising a first inflatable bag, the first inflatable bag delimiting said sterile operation chamber against the ambient environment. The first inflatable bag comprises a first and a second access opening to allow a user to insert a first and a second arm into the operation chamber, a chamber operation opening to allow access to said skin region of the patient out of the operation chamber, and a window for observing handling operations inside said sterile operation chamber. The first inflatable bag is coupled to a support frame, the support frame having a transport configuration and an operation configuration. In the transport configuration, the first inflatable bag is confined, such as to have compact dimensions, and in the operation configuration, the first inflatable bag is extended, such as to form said sterile operation chamber.

According to this aspect of the invention, a specific device is provided which allows to define and to confine a sterile space of limited size above a skin region of a patient. This sterile limited space can be accessed by a surgeon and by assistant personal through openings in the inflatable bag, whereby it is to be understood that such openings may be closed by elastically deformable means or a sealed glove with elongated/cuff arm sleeve may be attached to such an opening and a person reaching into the inner space of said inflatable bag may put his hand and arm into such sleeved glove. It is to be understood that further such openings may be provided in said inflatable bag, e.g. one or two additional pairs of such openings for assistant personnel.

Generally, the inflatable bag is comprised of a flexible sheet material like a flexible foil or the like. The flexible bag may be semitransparent or transparent to allow a person to watch and observe any handling operations inside said flexible bag and to provide a good illumination inside said bag by outer light sources arranged outside said inflatable bag. In particular, by such transparent properties a window may be provided in said inflatable bag but alternatively, such window may be inserted into a flexible bag made of a non-transparent or semitransparent material to allow visual inspection of the interior of the bag by a person from outside. In addition, said window may specifically be tailored to fit on imaging devices, like microscopes or other optical systems like cameras or an additional window for such purpose, may also be provided. Such window may comprise an adaptor ring which can be coupled to the objective of the imaging device.

The inflatable bag is connected to a support frame wherein said support frame may comprise a single or a plurality of frame members. The support frame may be arranged outside the flexible bag or inside the flexible bag and, in particular, if the support frame is arranged inside the flexible bag, the coupling of the support frame and the flexible bag may be comprised of a simple form locking arrangement of the flexible bag around the support frame without particular connections between the support frame and the flexible bag to allow a limited relative movement of the flexible bag versus the support frame. The support frame is intended to establish an operation configuration wherein a sterile operation chamber is formed inside the inflatable bag. In this operation configuration, the support frame provides a scaffold-like function to span the flexible bag into a tent-like configuration which may have a tube form, a bow form or the like. By this, an inner space is provided independently from any specific pressure condition like an increased pressure inside the bag and is maintained independently from any pressure source like a pressure pump, or the like. The sterile air volume in the inner space is drawn and released passively over appropriate sterile (HEPA or similar) filters by the expansion and collapsing of the support frame. The support frame can be collapsed to a transport configuration, wherein the inner volume inside said inflatable bag is significantly reduced, in particular collapsed to an inner volume close to zero such that in the transport configuration, the whole isolation device has a compact design such as a flat design which can easily be transported. To allow such collapsing from the operation configuration into the transport configuration the support frame may be made from elastically deformable frame members or may comprise stiff frame members connected to each other via elastically deformable hinges or the like. In particular, the support frame may comprise frame members having a biased cross-sectional configuration which can be transformed into a cross-sectional configuration allowing simplified bending of the frame members such as to establish a stiff, rigid support frame configuration in the operation configuration and a flexible, confined support frame configuration in the transport configuration.

It is to be understood that the isolation device may preferably be coupled to a sterilizing device as described beforehand. Such a combination of the isolation device and the sterilizing device may be provided as a package, e.g. a package with the isolation device in a confined, packed condition attached to the first or second frame. By this, the upper surface of the first or second foil is kept in a sterile environment and thus, a surgical treatment can immediately be started right after expanding the inflatable bag and disinfecting the skin.

According to a first preferred embodiment, support frame comprises hollow support frame members having at least one connector for introducing a fluid material into said support frame members, wherein in said transport configuration, said support frame members are deflated and slack and in said operation configuration said support frame members are inflated to a pressurized state such that the support members are rigid, or in said transport configuration, said support frame members are deflated and slack and in said operation configuration a curable liquid is inserted into said support frame member, said curable liquid being cured to a hardened condition. According to this embodiment, the support frame comprises or is composed of one or a plurality of hollow frame members and these hollow frame member(s) is deformable and slack in a deflated condition wherein no or low pressurized fluid is inside said hollow frame members and a rigid or stabilized condition, wherein the hollow frame members may be brought into a stiff and rigid configuration by two alternative functional measures. According to a first alternative, the hollow frame members are inflated by a pressurized fluid like a gaseous fluid, for example pressurized air, and thus are pumped into a stiff and rigid form. According to a second alternative, a curable fluid like a polymer liquid is inserted into the hollow frame members and undergoes a curing action, for example by a chemical reaction of said polymer liquid thus hardening inside the hollow frame members. This curing action may include a slight or significant expansion inside the hollow frame members thus further enhancing the stability of the support frame.

It is to be generally understood that the support frame may comprise one single or a plurality of support frame members wherein such plurality of support frame members may be interconnected with each other such that the pressurized fluid or the curable fluid may be inserted into all support frame members via one single connector only. In other embodiments, two or more support frame members may be provided each having a separate connector for inserting said fluid into the support frame members.

According to a further preferred embodiment of this aspect of the invention, said support frame is formed by a plurality of elastically joined rigid support frame elements. According to this embodiment, a plurality of stable and indeformable frame elements is provided which are joined to each other by swivable elastically deformable joints. It is general to be understood that according to the invention an elastically deformable material or component is understood as a component which can be transformed by a reasonable force from one geometrical configuration into a different geometrical configuration without damaging the material, whereas a rigid or stiff material or component is understood as a material which resists such deformation up to a significant force applied to the material/the component and will be damaged if loaded over such force and be deformed thereby.

According to a further preferred embodiment, in said operation configuration said support frame elements comprise a middle support frame element such as to support the inflatable bag in a middle section between the first and second access opening; a bottom support frame element arranged below the first and second access opening, and a top support frame element arranged above the first and second access opening. According to this embodiment, a specifically preferred geometrical configuration of the support frame is provided which allows a wide range of motion of a person conducting a surgical operation inside said inflatable bag by reaching his both arms through the first and second access opening. To this regard, the support frame is composed of a middle support frame element between the first and second access opening and a bottom and a top support frame element, wherein these bottom and top support frame elements are arranged below and above the access openings, respectively. In particular, this embodiment may be composed of two ring-like elements or open ring-like elements formed as C-elements in a symmetrical arrangement and being arranged around the first and the second access opening.

According to a still further preferred embodiment, the isolation device is further improved by an instrument chamber separate from said operation chamber and enclosed by a second inflatable bag coupled to a secondary support frame, wherein a transfer port is provided between the operation chamber and the instrument. According to this preferred embodiment, a second inflatable bag is provided which encloses an inner space serving as an instrument chamber. This second inflatable bag may have access openings for the arms of assistant personal to sort and grab the instruments and to don such instruments to a surgeon conducting a surgical operation in the first inflatable bag. To allow such donning and receiving interaction between the assistant personal's hands inside the second inflatable bag and the surgeon's hands inside the first inflatable bag a transfer port is provided between the first and the second inflatable bag.

Such transfer port may be defined by a frame element in the first inflatable bag and a corresponding frame element in the second inflatable bag wherein the two frame elements can be sealingly coupled to each other to define an inner opening between the two frame elements serving as a transfer port. Preferably, the frame elements define such an inner transfer opening which is initially closed by a foil such that the first inflatable bag and the second inflatable bag independently from each other define a sterilized inside volume and can be coupled to each other without the risk of migration of any non-sterile fluid into said interior space. After having been coupled sealingly to each other the foils closing the transfer port inside the frame elements may be removed or cut such that instruments or the like can be reached through the transfer port.

According to a further preferred embodiment the first inflatable bag comprises an operation chamber connection frame encompassing an operation chamber transfer opening; the secondary inflatable bag comprises an instrument chamber connection frame encompassing an instrument chamber transfer opening; wherein an operation chamber shutter foil is attached to the operation chamber connection frame, such as to provide a fluid-tight sealing of the operation chamber transfer opening; and an instrument chamber shutter foil is attached to the instrument chamber connection frame, such as to provide an fluid-tight sealing of the instrument chamber transfer. This specific embodiment allows for independent sterile inside volumes or spaces in the first and the second inflatable bag and a safe connection of such two separate inside volumes after coupling of the first and the second inflatable bag.

According to a further preferred embodiment, the operation chamber connection frame comprises an operation chamber connection surface facing the instrument chamber connection frame. The instrument chamber connection frame comprises an instrument chamber connection surface facing the operation chamber connection frame, wherein the operation chamber shutter foil comprises a operation chamber shutter protrusion. The instrument chamber shutter foil comprises an instrument chamber shutter protrusion. When the operation chamber connection surface and the instrument chamber connection surface are brought into fluid-tight contact and the operation chamber shutter foil and the instrument chamber shutter foil are removed by means of the operation chamber shutter protrusion and the instrument chamber shutter protrusion, respectively, the operation chamber transfer opening and the instrument chamber transfer opening form the transfer port between the operation chamber and the instrument chamber. This further preferred embodiment allows for a convenient opening and closing of the transfer port between the operation chamber and the instrument chamber and thus allows safe coupling and decoupling of the instrument chamber to the operation chamber. The option to close the transfer port after it had been opened to handle instruments trough the transfer port allows a decoupling of the instrument chamber and a coupling of a different instrument chamber to the operation chamber in the course of a surgical operation in order to provide new or different instruments to the surgeon depending on the needs and requirements of the ongoing surgical operation.

According to a further preferred embodiment, the operation chamber connection frame comprises at least one connection protrusion, extending from the operation chamber connection surface along a direction substantially perpendicular to the plane that is defined by the operation chamber connection frame; and wherein the instrument chamber connection frame comprises at least one connection groove, adapted to receive the at least one connection protrusion. According to this embodiment, a safe handling and a form locking engagement of the support frame of the operation chamber with the support frame of the instrument chamber is established thus preventing false arrangement and coupling action of the chambers.

According to a further preferred embodiment, a plurality of light sources is arranged at the support frame, in particular partially integrated into the support frame. According to this preferred embodiment, a direct illumination inside the inflatable bag is provided by illumination devices like LED light sources attached to or integrated into the support frame. This allows a convenient and strong illumination inside the inflatable bag without the risk of having shaded regions. According to the invention, an energy source for supplying energy to the light sources can be integrated into the isolation device, in particular can be integrated into the support frame to provide an independent isolation device from any other energy sources. Alternatively, an electrical connector or plug element can be provided at the isolation device, for example at the support frame to connect the isolation device to an external electrical energy device for supplying said light sources.

According to a further preferred embodiment, the isolation device according to the invention further comprises an opening in said first inflatable bag and a flexible hose defining an interior space, wherein said flexible hose is attached to said first inflatable bag along the circumference of said opening, said flexible hose being adapted to take up a device like a surgical instrument in its interior space and said flexible hose is made from a flexible material adapted to be wrapped around a longitudinal axis of said hose to establish a sealing in a wrapped region such as to seal a sterile interior space of said inflatable bag, wherein an inner transport space in said flexible hose, which is sealed such a wrapped region, can be moved from outside of said first inflatable bag into said sterile interior space of said first inflatable bag. According to this embodiment, a specific insertion unit is provided at said first inflatable bag allowing to introduce instruments or any other devices from outside the inflatable bag into the sterilized interior space inside said inflatable bag. Further, such unit can be used in a reverse direction to transfer material out of said sterilized interior space to the outside of the inflatable bag. The specific functionality of this insertion or discharging/exporting unit is a flexible hose attached to an opening in the first inflatable bag and generally sealing said opening in that the flexible hose is wrapped along its longitudinal axis to define a wrap sealing region. By this, the opening is kept closed in a usual condition, wherein no components are to be inserted or to be exported into/out of the sterilized interior space. However, in use, the components may be put into the hose and the hose may be wrapped to enclose the component and hereafter a transitional, longitudinal movement of the wrapped component through the opening together with the wrapped section of the hose may be performed such as to move the component from inside to outside or from outside to inside, respectively. Hereafter, the wrapping of the hose may be dewrapped such as to release the component out of the hose in case of inserting an instrument into the interior space. Further, the sealing provided by said wrap may be maintained, for example if any organic waste or the like is to be exported and kept sealed. Further the wrapping might be accomplished alternatively with two circumferential sealing clips to define one sealing region and allow cutting between the clips, thus sectioning and preventing an unwanted subsequent unwrapping. The advantage would be the individual and independent wrapping of components and their handling. A further sealing method would be accomplished with intermitted distanced adhesive tape sections in the inner part of the hose, which also would provide a tight sealing to blister packed items or inside the hose. Sterile access to the component would be possible by a controlled opening of such sealing clips or tape sealings which then may also effect opening of the adherent blister package or medication containers.

According to a further preferred embodiment, the first inflatable bag may comprise an opening, said opening being closed by a lock adapted to channel a container for surgical instrument into said first inflatable bag. Such a lock may be designed in different ways. In particular, the lock may comprise two rollers biased in close contact to each other and the container may be pushed through the two rollers and at the same time the rollers may be adapted to disconnect and wrap a foil covering the top side of the container such as to maintain a sterile environment inside the container and opening the container upon insertion of the container through the lock into the interior sterilized space inside the bag. Alternatively any instrument trays inside the container may be fully enclosed by a steam permeable bag which has a removable lid, which is fitting to the lock. Thus, only the inner part of the container may be pushed through the rollers whereas the container itself remains outside of the sterile space.

According to a further preferred embodiment the first inflatable bag may comprise a lower frame coupling element for coupling the first inflatable bag with a device for producing and maintaining a sterile surface on a patient's skin as explained beforehand, in particular with the first frame element or with the second frame element of the said device. By this, the isolation device can be perfectly used in connection with the convenient device for producing the sterile surface on the patient's skin. In particular, such a device can be part of the inflatable bag such that the first frame or the second frame is attached to the inflatable bag and thus, upon attaching the first frame to the patient's skin, a sterile interior space inside the inflatable bag can be opened to the patient's skin after it has been sterilized by the flooding action with the sterilizing agent as described beforehand.

Still further, it is to be understood that inside the isolation device an assisting device for facilitating the taking on and taking off of a surgical glove can be arranged. In particular, a plurality of such assisting devices including a surgical glove can be arranged inside the inflatable bag such as to allow a surgeon to take on such surgical gloves when reaching through the access ports into the inflatable bag.

According to a further aspect of the invention it is provided a device for introducing sterile instruments into an operation chamber or an instrument chamber, comprising an introduction frame; a first roller and a second roller arranged rotatable around their respective longitudinal axis, and attached to said introduction frame, such that the longitudinal axis of the first roller and the longitudinal axis of the second roller are parallel, wherein the first roller and the second roller are further attached to said introduction frame such as to be movable along an axis extending perpendicular to their respective longitudinal axis; wherein a distance between the first roller and the second roller is determined by a position of a movement of the first and second roller along the axis extending perpendicular to the longitudinal axes, and wherein said first and second rollers are biased versus each other to contact each other and said first and second roller can be moved along said axis to increase said distance to allow insertion of an instrument through a gap provided by said distance.

According to this aspect of the invention, an improved device for introducing sterile instruments into an operation chamber or an instrument chamber is provided. The device comprises a first and a second roller which in a non-use condition sealingly engage with each other in that the two rollers are biased against each other. The two rollers are rotatably arranged in a frame and can conduct a rotational movement against said frame. At least one of the two rollers can further be moved against said frame in a direction perpendicular to its rotational axis such as to establish a gap to the other roller. This movement can be a linear sliding movement or a movement along a curve or the like. According to the invention, by such a movement of one of the rollers or the both rollers will provide a gap between the rollers and an instrument may be inserted through such gap. The instrument may preferably be in a blister package of two flexible foils and in such case, the rollers are adapted to take up these foils in such a way that the upper roller takes up the upper foil and the lower roller takes up the lower foil. As an example for such specific embodiment, a longitudinal slit may be provided inside the rollers and an edge end region of the upper and the lower foil may be inserted into the slit of the upper roller and the lower roller, respectively. In such case, if the instrument is inserted by establishing a small gap between the rollers and pushing the blister package with the instrument through said bag by a rolling action of the rollers, the blister package is torn open and the instrument is pushed through the two rollers. By this, a sterile environment on the one side of the two rollers can be maintained whereas on the other side of the rollers a non-sterile environment may be present.

The so defined device is particularly well suited for being connected to a flexible bag of an isolation device as described beforehand so as to allow insertion of instruments into the interior sterilized space inside such inflatable bag.

According to a preferred embodiment of this aspect of the invention, said first roller is adapted to wrap up an upper foil of a sterile blister packaging of said instrument and said second roller is adapted to wrap up a bottom foil of the sterile blister packaging upon insertion of said instrument through said gap in the blister packaging.

According to a further preferred embodiment, the device may be further improved by a box for receiving the instrument inside the operation chamber or the instrument chamber. Such a box or container may prevent an instrument being inserted into an inflatable bag to get lost or to fall onto the patient's skin or the like.

It is particularly preferred that said introduction frame is attached to a first or second inflatable bag of an isolation device as described beforehand.

According to a further aspect of the invention, it is provided a mechanical cabinet for storing of instruments inside an operation chamber or an instrument chamber, comprising: a shelf frame; a storage area and an extraction area; and at least one shelf movably, in particular pivotably affixed to the shelf frame, such as to be moved or pivoted, respectively from the storage area into the extraction area and from the extraction area into the storage area.

The so defined mechanical cabinet is particularly suited for storing a plurality of instruments or devices for conducting a surgical operation in a quite limited space like for example inside an inflatable bag defining a confined and limited sterilized volume above a skin region of a patient. A specific problem related to operating procedures conducted in such an environment is the limited space defined by such an inflatable bag and the need to preferably provide all instruments required for conducting the surgical operation inside said inflatable bag. In such a situation, it is preferable to arrange a mechanical cabinet inside the inflatable bag and to store and present the instruments and any further devices required for the operation on the shelves of the mechanical cabinet. The surgeon or assistant personal may then conveniently move one shelf or a plurality of shelves relative to the shelf frame to allow easy access to the instruments positioned on the shelves.

According to a preferred embodiment, at least one shelf rigidly affixed to the shelf frame, the at least one rigidly affixed shelf being spaced from the at least one movably affixed shelf by a predefined distance. According to this embodiment, one rigid shelf will help defining a stable standing of the mechanical cabinet and one movable shelf will allow to significantly increase the storage capacity of the mechanical cabinet and allow simple access to the instruments.

Still further, it is preferred that the mechanical cabinet further comprises at least one, preferably two vertically disposed and synchronously driven endless chains, wherein the at least one shelf is affixed in a substantially horizontal orientation of an upper surface of said shelf to the endless chain(s). According to this embodiment, the shelves are arranged in a horizontal extension such that the instruments and devices can be positioned onto the shelves and kept thereon by gravity force and the shelves can be moved in such a way as to maintain its horizontal orientation. In this embodiment, the shelves are arranged and moved like the cabins in a paternoster lift design and thus significantly improve the capacity for storing instruments inside a limited space by at the same time allowing simplified and quick access to the instruments.

According to an alternative embodiment, the at least one pivotably affixed shelf is mounted to said vertically arranged shaft or axis for a pivotal movement around said shaft or axis, respectively; and wherein the at least one pivotably mounted shelf comprises holding means for releasably holding of the instruments on said shelf. In this embodiment, the shelves are arranged in a vertically extended arrangement such as to define vertically extending surfaces for positioning the instruments and devices thereon. It is to be understood that in such case the instruments cannot be positioned and fixed on the shelves by gravity force but rather specific holding means must be provided on the shelves for releasably holding the instruments on the shelves. In this particular embodiment the shelves are arranged like the pages of a book standing upright on a surface and the shelves can be moved around a vertical axis in the same way as the pages of an upright book can be scrolled or skimmed through.

According to this preferred embodiment it is further preferred that said holding means are selected from: (a) magnetic means incorporated into said shelf, (b) hooks attached to said shelf, (c) openings in said shelf. According to this further preferred embodiment, specific means are provided on said shelves to fix the instruments or devices on the shelf, wherein it is understood that preferably all three different means for fixing the instruments or devices on the shelves are provided on each shelf to allow a variability with regard to different instruments and devices.

According to a further preferred embodiment, the mechanical cabinet can be further improved by a plurality of movable shelves to improve and increase the capacity for storing instruments and devices.

Still further, it is to be understood that the isolation device described beforehand may be further improved by arranging a mechanical cabinet as described beforehand inside the first or the second inflatable bag. This will allow to provide and offer a large number of instruments and devices to a surgeon conducting a surgical operation using such an isolation device.

Still further, an aspect of the invention is the use of such a mechanical cabinet as described beforehand in an operation or an instrument chamber, in particular in an instrument chamber as described beforehand.

As regards the advantages, embodiment variants, and embodiment details of the method according to the present disclosure and its possible further developments, reference is made to the description provided herein of the respective features, as will be understood and appreciated by those skilled in the art upon studying the following specification, claims, and appended drawings.

BRIEF DESCRIPTION OF THE DRAWINGS

Preferred embodiments of the invention are described with reference to the enclosed figures. In the figures:

FIG. 1 is a perspective view of a sterilizing device according to an embodiment of the invention;

FIG. 2 is a cross-sectional view of the sterilizing device according to FIG. 1;

FIG. 2a is a detailed view of FIG. 2;

FIG. 3 is a schematic cross-sectional view of an isolation device according to an embodiment of the invention;

FIG. 4a is a perspective view of a first configuration of an assisting device according to an embodiment of the invention;

FIG. 4b is the embodiment according to FIG. 4a in a second configuration;

FIG. 5a is a schematic cross-sectional view of the assisting device in the first configuration according to FIG. 4a;

FIG. 5b is a view according to FIG. 5a in a second configuration according to FIG. 4b;

FIG. 6a is a perspective view of an assisting device according to a second embodiment of the invention in a first configuration;

FIG. 6b is the embodiment according to FIG. 6a in a second configuration;

FIG. 7a is a cross-sectional view of the embodiment according to FIGS. 6a, 6b in a first configuration;

FIG. 7b is the embodiment of FIG. 7a in a second configuration;

FIG. 9 is an introducing device in a schematic, side-sectional view according to one preferred embodiment of the invention;

FIG. 10 according to a first preferred embodiment of the invention in a schematic perspective view;

FIG. 11 is a mechanical cabinet according to a second preferred embodiment of the invention in a schematic side view;

FIG. 12b is another perspective view of the embodiment of FIG. 12a;

FIG. 13b is another perspective view of the embodiment of FIG. 13a;

FIG. 15b is another perspective view of the embodiment of FIG. 15a; and

DETAILED DESCRIPTION OF THE PREFERRED EMBODIMENTS

Figure 8:
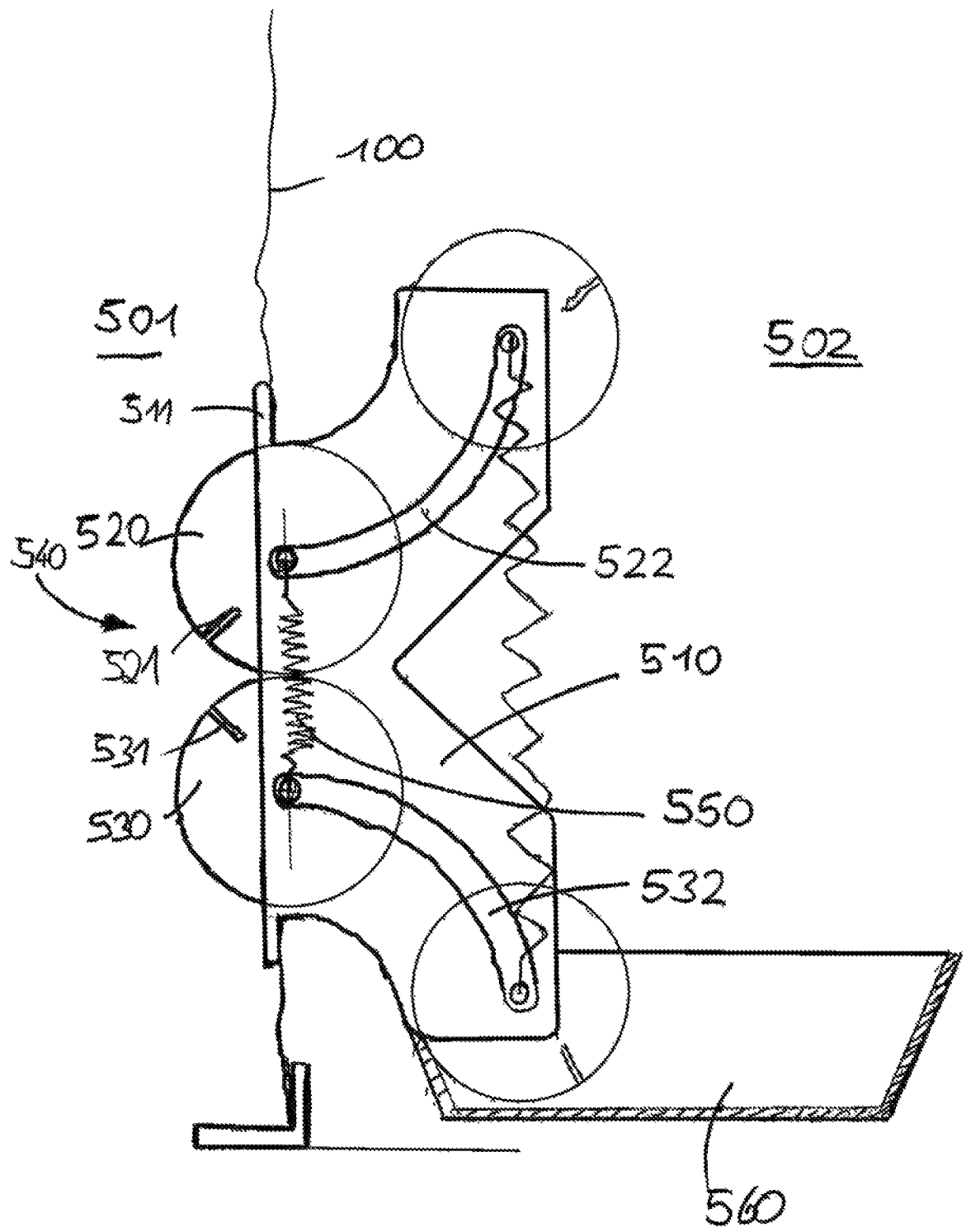
FIG. 8 is an introducing device according to a preferred embodiment of the invention in a schematic side view.

As referenced in the Figures, the same reference numerals may be used herein to refer to the same parameters and components or their similar modifications and alternatives. For purposes of description herein, the terms "upper," "lower," "right," "left," "rear," "front," "vertical," "horizontal," and derivatives thereof shall relate to the present disclosure as oriented in FIG. 1. However, it is to be understood that the present disclosure may assume various alternative orientations and step sequences, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise. The drawings referenced herein are schematic and associated views thereof are not necessarily drawn to scale. Identical elements or elements with essentially the same or similar function are referred to with the same reference number in the figures.

Referring first to FIGS. 1, 2, and 2a, a device for producing and maintaining a sterilized surface on a skin of a patient is shown in these figures in a preferred embodiment of the invention. The device comprises a first frame 10 of rectangular shape being composed of four linear frame members 11a-d which are joined to each other at the corners of the frame. The frame members 11a-d of the first frame generally have an L-shaped cross-section and are arranged in such a way that one leg of the L-shaped cross-section lies in a horizontal plane 1. Generally, the first frame 10 maybe composed of different profiled frame members, e.g., a U-shaped cross-section or a rectangular cross-section maybe used to form the first frame, as well.

The first frame defines a lower adhesion surface 12 in the horizontal plane 1 which can be attached to the patient's skin. The frame members surround an inner opening 20 of rectangular shape which is the opening serving the surging to conduct the surgical operation.

A first foil 30 is provided at the first frame 10 and covers the whole inner opening 30 being attached or coupled to the frame members 11a-d of the first frame on all four sides. As can be seen in FIG. 2a, the first foil 30 reaches through a slit 13 in one frame member 11a and a handle 31, preferably including an opening 32, is provided on the side of the first foil 30 protruding sideways out of the first frame. The handle 31 allows a user to pull out the first foil 30 out of the first frame after a sterilizing procedure has been accomplished.

In at least one region, the first foil 30 is in a short distance to the lower adhesion surface 12 of the first frame to the skin. In other regions, the first foil 30 may lay in the plane of the adhesion surface. Thus, a small sterilizing space is defined between the first foil 30 and the skin of the patient if the first frame is attached to the skin and the first frame.

A first channel 40 with a first connector 41 is arranged in the frame member 11b of the first frame and reaches through the frame member. The first connector 41 has an outer connector dimension of circular cross-section allowing to adapt a standardized connector to the first conduit like a luer lock or the like. The first channel 40 opens into the space established between the first foil 30 and the skin of the patient with an elongated cross-section, such as to be adapted in cross-section to the small distance between the first foil and the skin of the patient.

A second fluid channel 50 with connector 51 is provided in frame member 11d in the opposite corner region to the first channel 40. The second channel 50 is designed in a similar manner as the first channel 40 and connector 41. Whereas the first channel 40 serves to insert a sterilizing agent from outside the frame into the space between the first foil 30 and the skin of the patient, the second channel 50 serves to remove such sterilizing agent after a certain activating time when a complete sterilization of the skin of the patient and of the bottom surface of the first foil 30 has been reached.

A second frame 60 is provided and composed of four L-shaped frame members 61a-d. The second frame 60 has a slightly smaller dimension than the first fame 10 such as to allow the second frame 60 to be inserted into the first fame 10. As can be seen in detail in FIG. 2a, the second frame 60 is in sliding and sealing contact to the inner wall surface of the upright L-shaped lack member of the first frame members. A second foil 70 is spanned across the opening in parallel arrangement to the first foil 30 and attached to the lower end of the second frame 60. Thus, after the sterilizing process has been accomplished and the first foil 30 has been removed by pulling the handle 31, the second frame 60 can be pushed downwards to bring the second foil 70 in contact with the skin. The second foil 70 has a lower adhesive surface 71 to adhere and firmly attach to the skin of the patient thus establishing a protective cover on the skin in the region of the surgery and the incision. An edge region 71a is adapted to establish a stronger attachment to the patient's skin than the rest of the adhesive surface 71.

Generally, it is to be understood that both the first frame 10 and the second frame 60 can be collapsed in such a way that the legs of the L-shaped profiles of the frame members can be brought from the rectangular arrangement to each other to a parallel arrangement to each other wherein the legs lie directly onto each other.

The sterilizing device shown in FIGS. 1, 2, and 2a is generally well-suited to be used as an independent device for conducting a safe and quick sterilizing action of a skin region of a patient prior to a surgical operation. In particular, the sterilizing device can be used in connection with an inflatable bag defining a limited sterilized space above, such a skin region. For this purpose, such an inflatable bag may be attached to the first frame 10 or the second frame 60 in a sealing engagement and may in particular be clamped and firmly attached to the first and/or second frames 10, 60, by adhesive effects after the first frame 10 and second frame 60 has been collapsed.

FIG. 3 shows a sterilizing device comprising such an inflatable bag 100 according to a preferred embodiment of the invention. As can be seen, a sterilizing device comprising first and second frames 10, 60 according to FIG. 1 can be attached to the bottom cross-section of the inflatable bag as schematically shown in FIG. 3.

The device shown in FIG. 3 generally comprises an inflatable bag 100 which may have a dome-shaped geometry, as shown in the figure, but may alternatively have different other geometries. The inflatable bag 100 is coupled to two separate frame work members 110, 120 which define and maintain a specific geometry of the inflatable bag 100 independently from a specific pressure condition inside of the inflatable bag 100. Illuminating devices 111, 112, 121, 122 are arranged at the framework members 110, 120 to illuminate the inner space inside the inflatable bag 100.

An upper window region 101 is made of a fully crystal clear transparent material to allow precise observation of any handling processes inside the inflatable bag 100.

The inflatable bag 100 further comprises access ports 105, 106 in the inflatable bag 100. The access ports 105, 106 are combined with sleeves and gloves to define a sealed interior space, but allows a surgeon or assisting personnel to reach into the inner space from outside the inflatable bag 100.

Still further, an introducing and exporting device 130 is provided in the inflatable bag 100 at the lower bottom region. This introducing and exporting device comprises two rotatable rollers 131, 132 which can be moved apart from each other to open a gap between the rollers 131, 132 allowing the surgeon or assisting personnel to introduce instruments or the like from outside into the interior space. This introducing and importing device 130 is specifically adapted to conduct such an insertion or exporting action without affecting the sterile environment inside the inflatable bag 100 even if outside a non-sterile environment is present outside the inflatable bag 100. The insertion and exporting device 130 is explained in further detail hereafter with reference to FIG. 8.

In a first configuration, FIG. 4a shows an assisting device 200 for taking off and putting on a surgical glove. The assisting device 200 is shaped like a pouch and has a flattened configuration, as shown in FIGS. 4a and 5a. As can be seen, a surgical glove 250 can be inserted into the interior 210 of a fluid-tight wall defining the pouch-like geometry of the assisting device 200. The surgical glove 250 is reversed in its cuff region 251 and thus engaged sealingly with the edge 211 of an opening 220 on one side of the pouch. Generally, alternatively to this reversing and thus sealingly engaging of the cuff region 251 of the surgical glove 250, other mechanisms may be used to sealingly engage the cuff region 251 of the glove to the fluid-tight wall 200 in the edge region 211 of the opening 220.

The fluid-tight wall 200 may be deformed from the flattened configuration with an approximately elliptical cross-sectional shape, as shown in FIGS. 4a, 5a, to an enlarged shape with a cylindrical cross-section, as shown in FIGS. 4b, 5b. In this enlarged second configuration, the inner space 210 of the fluid-tight wall is significantly increased compared to the size of the inner space in the first configuration shown in FIGS. 4a, 5a. Thus, in a space region 210a, which is sealingly enclosed by the fluid-tight wall and the surgical glove 250, a low pressure is established and since on the other side, namely inside the glove 210b, atmospheric pressure is present, this effects a stretching and enlarging of the surgical glove 250 in the second configuration. The enlarged dimension of the surgical glove 250 in the second configuration can be seen in FIG. 5b. As will be understood, a person intending to put on the surgical glove 250 may now easily slide his hand into the surgical glove 250 and may thereafter return the assisting device into the first configuration, thereby tightly attaching the surgical glove 250 to his hand and thereafter remove his hand from the assisting device. In the same way, a person with the surgical glove 250 on his hand may slide his hand into the assisting device in the first configuration, establish a sealing contact to the edges of the first opening, e.g., by reversing the surgical glove 250 in the cuff region 251, as shown in the figures, or in any other ways, and thereafter deform the fluid-tight wall into the second configuration to thereby enlarge the surgical glove 250 and pull the surgical glove 250 away from the hand to remove the hand from the surgical glove 250 and the assisting device in said second configuration. This easily allows removing the surgical glove 250 from a hand without the need of contacting any contaminated surfaces of the surgical glove 250.

FIGS. 6a, 6b, 7a, sand 7b show a second preferred embodiment of an assisting device for putting on and removing the surgical glove 250. The device comprises a first, tube-like component 310 and a second, cup-like component 320 which is inserted into the first component 310. Both components 310, 320 have a similar cross-sectional geometry whereas the first component 310 is dimensioned slightly larger than the second component 320. The first component 310 is open at both ends and defines an opening 330 at one side of the device. The second component 320 is open at one end only and is arranged such as to be open towards the opening 330 on one side of the device as well but is closed by a bottom lid 321 on the other side. The second component 320 sealingly engages the first component 310 by a circumferential sealing lid 322 arranged at the front end region of the second component 320 close to the opening of the second component 320. As can be seen in FIGS. 6a, 6b and 7a, 7b, the second component can 320 be moved in a sliding movement in an axial direction in relation to the first component 310.

A surgical glove 350 can be attached sealingly to the opening 330 of the first component 310 and may reach into an interior space 340 defined by the first and second components 310, 320. By this, the interior space 340 is divided into a completely sealed region 340a against the atmosphere by the first and the second components 310, 320, and the surgical glove 350 and a region 340b inside the surgical glove 350. FIGS. 6a, 7a show the assisting device in a first configuration wherein the inner space 340 has a first volume size. As can be seen in FIGS. 6b, 7b, when sliding the second component 320, such as to elongate the total length of the assisting device, the inner space 340 is significantly increased by the telescoping movement of the first and the second components 310, 320 relative to each other. By this, a vacuum is established in the space region 340a effecting a significant enlargement of the surgical glove 350 being under atmospheric pressure in the space region 340b. By this, the surgical glove 350 is significantly increased and thus maybe put on or removed conveniently by a user.

FIG. 8 shows a device for inserting and exporting articles, like instruments or medical devices, from a first non-sterile environment 501 into a second sterile environment 502, and vice versa. The device is particularly adapted to be incorporated into an isolation device as described beforehand.

As can be seen, the device comprises a frame 510 having a flange 511 which can be mounted to the inflatable bag 100 in a sealing arrangement. In the frame 510, two rollers 520, 530 are mounted rotatably along its longitudinal axis. The rollers 520, 530 are shown in a closed condition of the device and in this condition the rollers 520, 530 are in contact to each other and in contact to the frame 510 to completely seal an opening 540. In this closed condition, the rollers 520, 530 are biased versus each other by a spring 550.

The axis or shafts of the rollers 520, 530 are positioned in a curved groove or curved opening 521, 531, respectively.

The curved grooved/openings 522, 532 allow the two rollers 520, 530 to slide along a curved travel path wherein the two rollers 520, 530 are pushed away from each other, thus giving an insertion/exporting opening between the two rollers 520, 530. As can be seen in dashed lines when being pushed towards the end the travel path, the two rollers 520, 530 give way for an instrument or a device having the size of the opening 540 as a maximum dimension.

By this, an instrument or device may be pushed from the left side in FIG. 8 to the abutting region of the two rollers 520, 530, thus pushing the two rollers 520, 530 away from each other and allowing the insertion of the device/instrument from the left side to the right side. The instrument may thereafter be taken up in a container 560 on the right side.

The device shown in FIG. 8, in particular, allows a sterile incursion of instruments from a non-sterile environment on the left side of the device to a sterile environment on the right side of the device. This is conducted by instruments or devices being contained in a blister package. Both rollers comprise a slit 521, 531 wherein the end edge regions of such two foils defining such a blister package can be inserted. When pushing such instrument in such blister package through the gap between the two rollers 520, 530, the blister package is torn open and the two foils defining the blister package are wrapped around the rollers 520, 530. By this, the instrument is released out the blister package into the environment 502, but at the same time the gap between the two rollers 520, 530, which is open for the time of the insertion, is kept sealed against environment 501 by the blister package being wrapped around the two rollers 520, 530.

As can be seen, the two rollers 520, 530 are pushed or drawn back into the closed position by the spring 550 after such an insertion procedure.

FIG. 9 shows a device for inserting or exporting objects into or out of a controlled environment, such as a sterile environment, by a simple mechanical set up. A frame 610 defines an opening 620, e.g., a circular opening. The frame 610 may be attached to an inflatable bag 100 or the like which separates a controlled atmosphere, such as a sterile environment, against the outside.

A flexible hose 630 is attached to the frame and has a certain length. The flexible hose 630 may extend to one side with a first portion 631, may then be reversed to be directed to an opposite direction with a second portion 632, and have a wrapped portion 633, wherein the flexible hose 630 is wrapped around its own to define a sealing. In a portion 634, an object 640, e. g. infectious waste or the like, may be positioned and may be sealed on both sides by such wrappings in hose regions 633, 635. A remaining length portion 636 of the flexible hose 630 may be used to further seal such objects with additional wrap regions. By this, the flexible hose 630 may be used to seal multiple such objects and to allow transfer of such objects from the inside to the outside, or vice versa, by moving the flexible hose 630 through the opening 620.

FIG. 10 shows a mechanical cabinet for storing instruments thereon. The mechanical cabinet generally comprises a vertical axis 710, which is mounted on a base plate 720 for standing upright in a stable position. Three sheets 731, 732, 733 are mounted to the axis 710 in a rotatable manner such as to rotate around the vertical axis 710. By this, the sheets 731, 732, 733 can be rotated so as to allow a user to access any instruments clipped or hooked to any of the sheets 731, 732, 733 in a simple way. Generally, the vertical axis 710 may be a shaft, and the sheets 731, 732, 733 may be mounted rigidly to the shaft wherein the shaft itself is mounted rotatably in a bearing 711 on the bottom side. Alternatively, the vertical axis 710 may be an axle, and the sheets 731, 732, 733 may be mounted to said axle in a rotatable manner via bearings or the like (not shown). It is to be understood that one of the sheets may be mounted rigidly to the base plate to increase stability of the whole construction whereas the other sheets may be mounted rotatably. Further, it is to be understood that instead of having three sheets there may be only two sheets, or four sheets, or even more than four sheets.

FIG. 11 shows a further preferred embodiment of a mechanical cabinet for storing multiple instruments and devices in a limited space. The device comprises a number of six sheets 810a-f, but other numbers of sheets, such as three, four, five, seven, eight or even more, may be provided. The sheets 810a-f are mounted to a moving mechanism, e. g., a frame, having a curved groove or opening or a lever mechanism allowing to move the sheets 810a-f along a curved path 830 in a closed loop. Generally, the sheets 810a-f are positioned inside the frame in such a way that they always keep a horizontal orientation and which may be achieved by a swinging mounting of the sheets 810a-f inside the device and keeping the orientation by gravity, or it may be achieved by lever mechanisms wherein two levers are defining the motion of each sheet and thus maintain such horizontal orientation by a parallelogram arrangement or the like.

The sheets 810a-f are adapted to receive instruments, devices, or the like on the top surfaces and allow a user to simply access such instruments by moving the sheets 810a-f into a position wherein those instruments required by the user are accessible from the respective sheet. It is to be understood that the sheets 810a-f may be movable independently from each other or may be interconnected to each other such that a synchronous movement of the sheets is possible.

The moving mechanism, like the frame defining the travel path of the sheets, is mounted to a base plate 820 for a safe and secure standing of the mechanical cabinet.

Generally, the mechanical cabinet shown in FIGS. 10 and 11 is perfectly suited for being used inside an inflatable bag, in particular in inflatable bag of an instrument chamber for conducting a surgical operation.

Figure 12A:
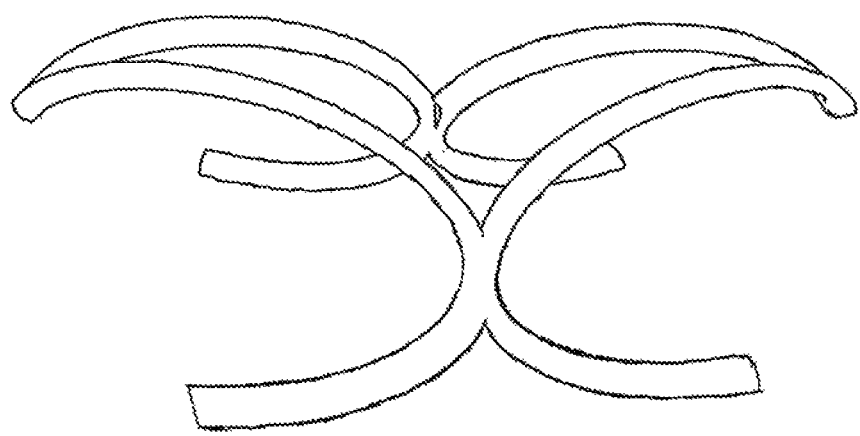
FIG. 12a is a schematic perspective view of a second preferred embodiment of a framework for an isolation device according to FIG. 3.
Figure 12B:
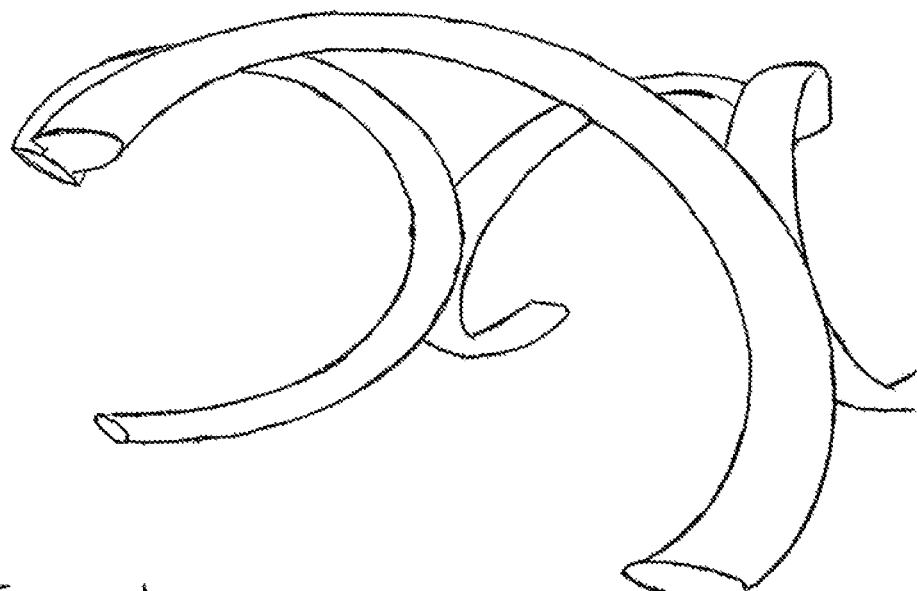

FIGS. 12a, 12b show a second preferred embodiment of a framework for an isolation device according to FIG. 3 having four, bow-shaped frame members in a twofold symmetrical arrangement.

Figure 13A:
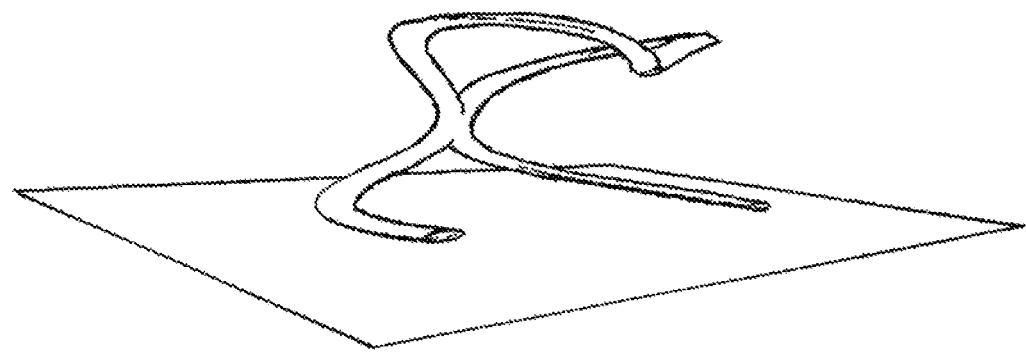
FIG. 13a is a schematic perspective view a third preferred embodiment of a framework for an isolation device according to FIG. 3.
Figure 13B:
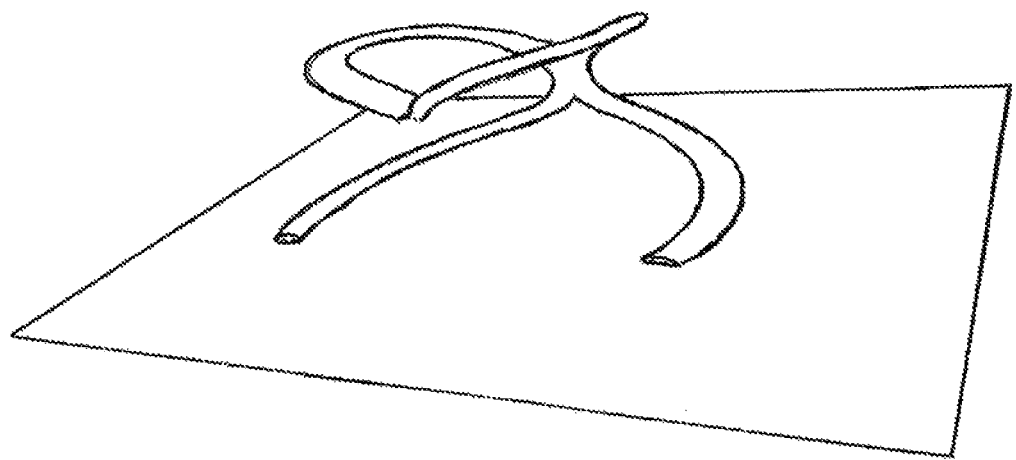

FIGS. 13a, 13b show a third preferred embodiment of a framework for an isolation device according to FIG. 3 having two curved frame members in a symmetrical arrangement and being open towards one side.

Figure 14:
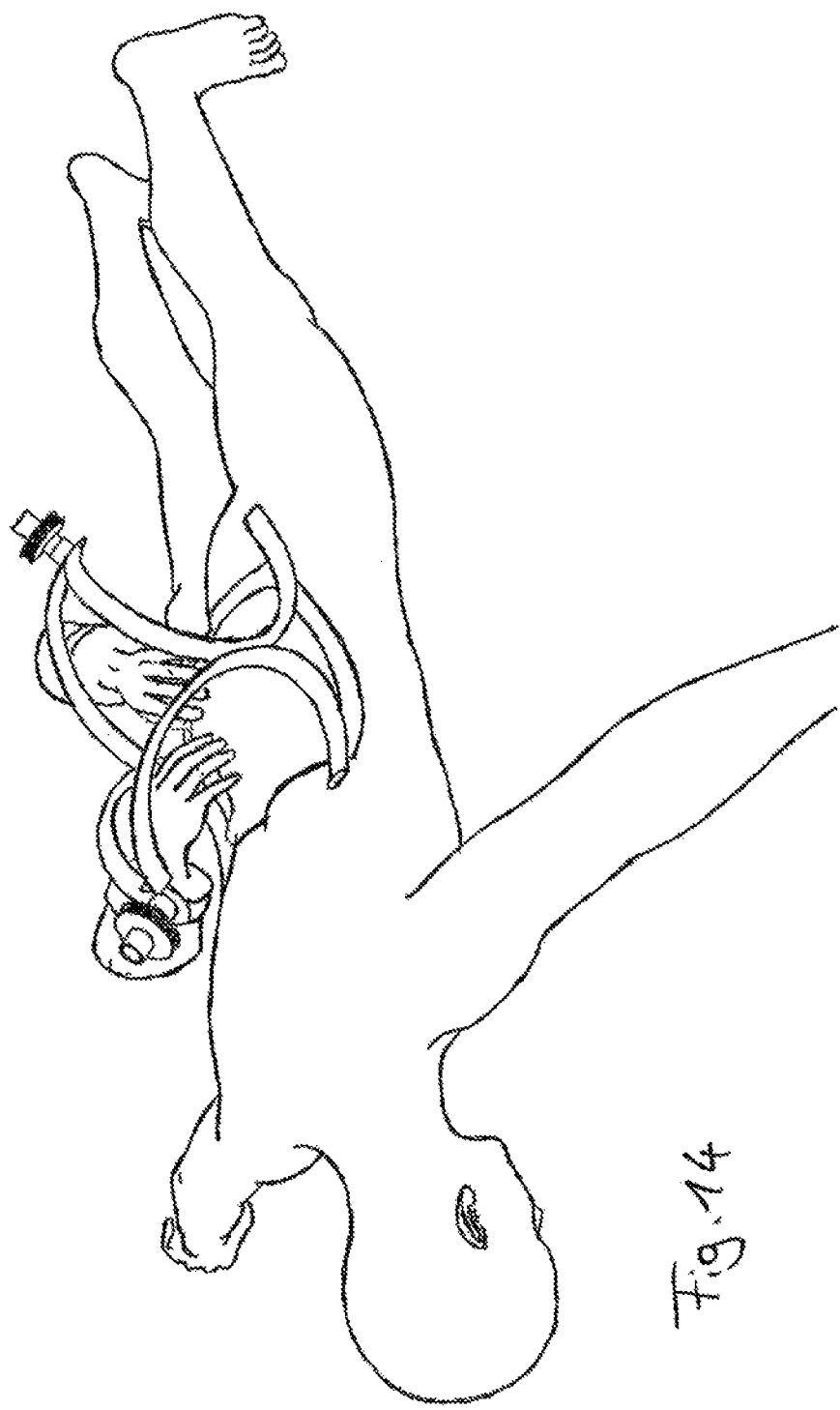
FIG. 14 is a perspective schematic view of an isolation device in use for a spine surgery.

FIG. 14 shows an isolation device with the inflatable bag 100 left away for better understanding in application for a spine surgery.

Figure 15A:
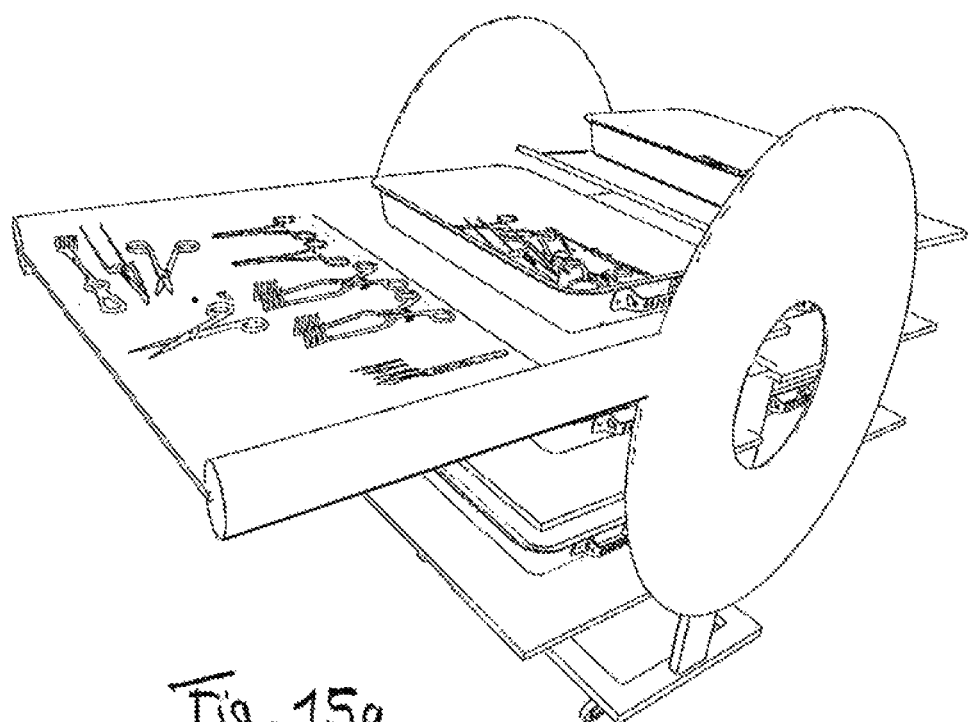
FIG. 15a is a perspective view of a third preferred embodiment of a mechanical cabinet.
Figure 15B:
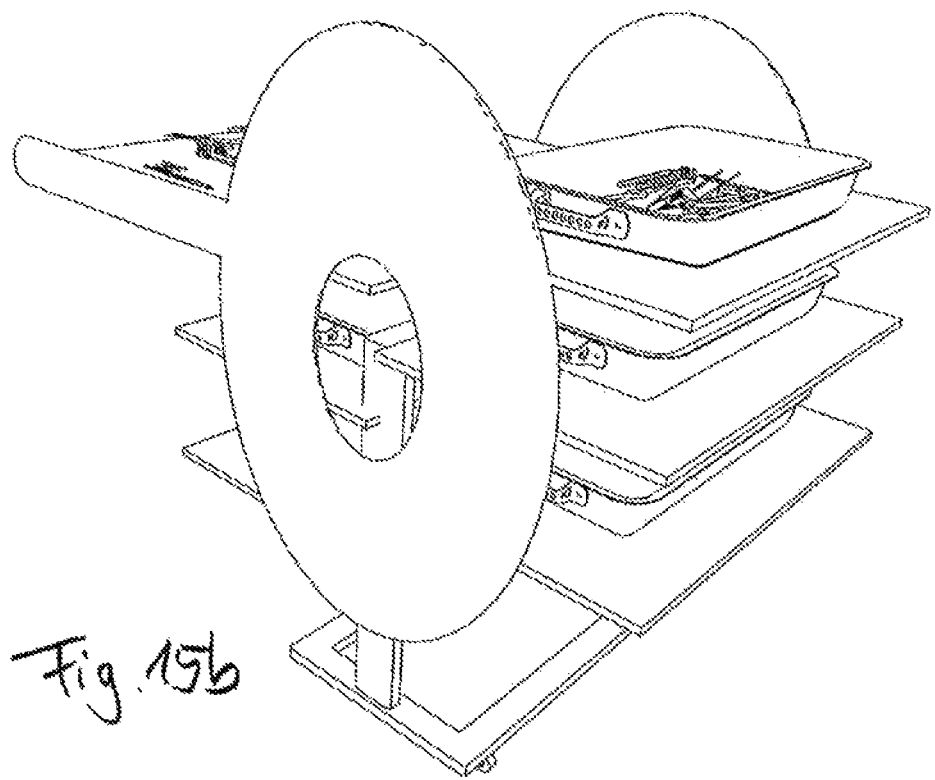

FIGS. 15a, 15b show a second preferred embodiment of a mechanical cabinet according to a paternoster arrangement.

Figure 16A:
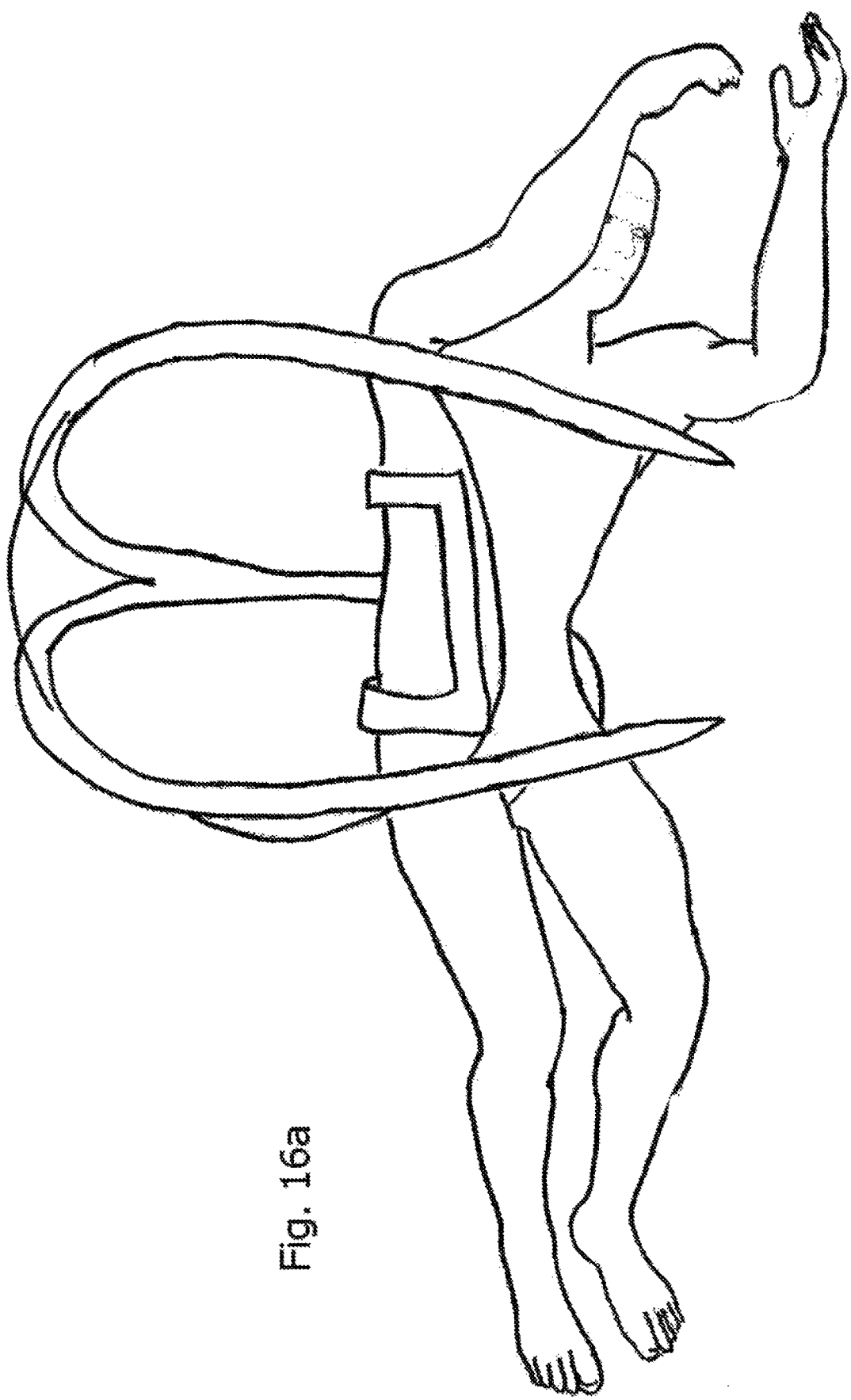
FIGS. 16a, 16b are two perspective schematic views of a further preferred embodiment of an isolation device in use for a lateral spine surgery.
Figure 16B:
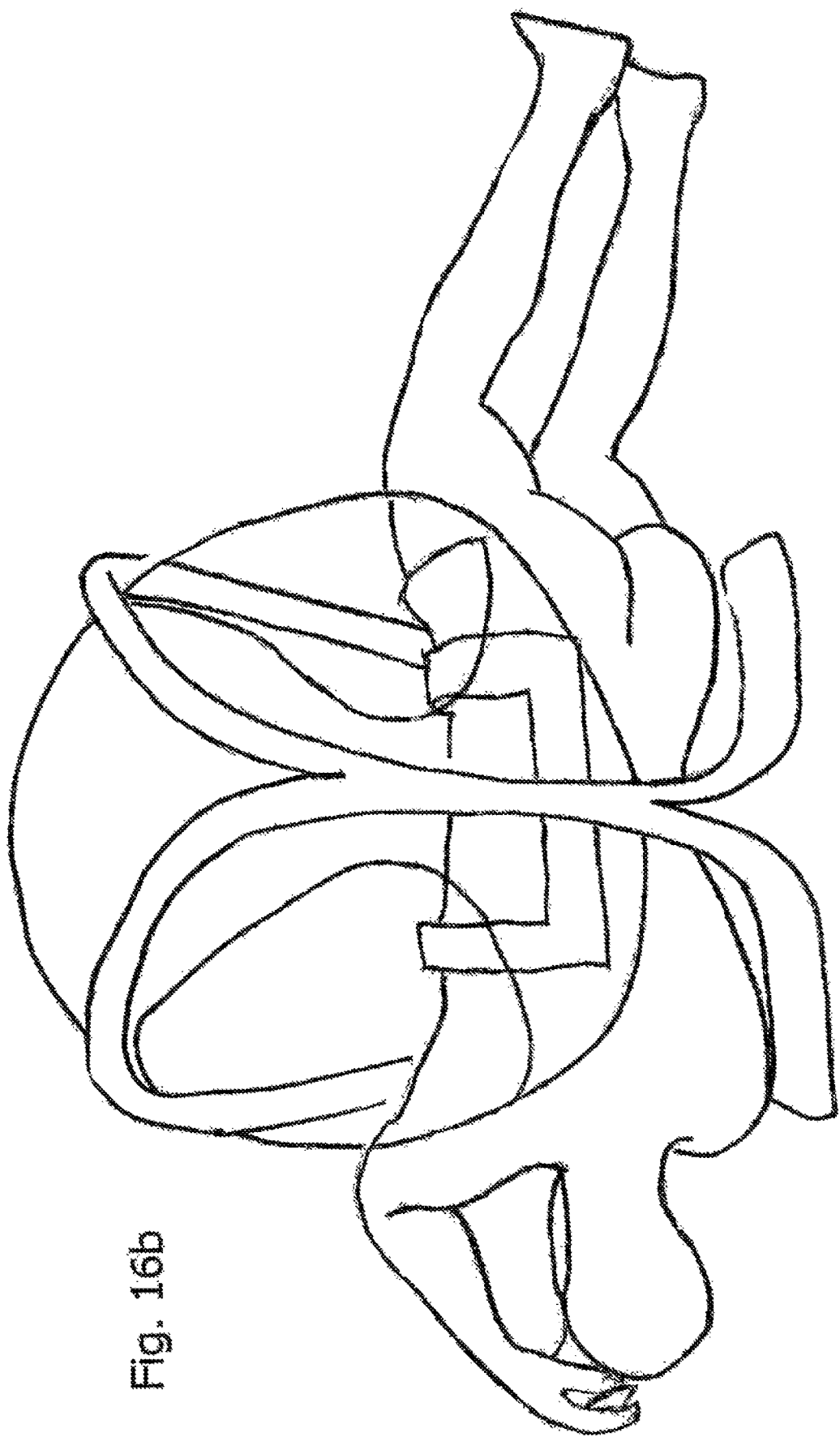

FIGS. 16a, 16b show a further preferred embodiment of an isolation device in use for a lateral spine surgery with the patient lying on his side. As can be seen, in this embodiment the frame of the isolation device is not supported on the skin of the patient but is rather supported onto the operation table. Preferably, the frame is arranged mainly or completely outside of the inflatable bag, i.e., it is not arranged in the inner sterile space defined by said inflatable bag.

It will be understood by one having ordinary skill in the art that construction of the described present disclosure and other components is not limited to any specific material. Other exemplary embodiments of the disclosure disclosed herein may be formed from a wide variety of materials, unless described otherwise herein.

For purposes of this disclosure, the term "operably coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

For purposes of this disclosure, the term "operably connected" (in all of its forms, connect, connecting, connected, etc.) generally means that one component functions with respect to another component, even if there are other components located between the first and second component, and the term "operable" defines a functional relationship between components.

It is also important to note that the construction and arrangement of the elements of the present disclosure as shown in the exemplary embodiments is illustrative only. Although only a few embodiments of the present innovations have been described in detail in this disclosure, those skilled in the art who review this disclosure will readily appreciate that many modifications are possible, e.g., variations in sizes, dimensions, structures, shapes and proportions of the various elements, values of parameters, mounting arrangements, use of materials, colors, orientations, etc. without materially departing from the novel teachings and advantages of the subject matter recited. For example, elements shown as integrally formed may be constructed of multiple parts or elements shown in multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of the wide variety of materials that provide sufficient strength or durability, in any of the wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is to be understood that variations and modifications can be made on the aforementioned structure and method without departing from the concepts of the present disclosure, and further it is to be understood that such concepts are intended to be covered by the following claims unless these claims by their language expressly state otherwise.

The invention claimed is:

1. A device for producing and maintaining a sterile surface on a patient's skin comprising:

a first frame having first frame elements encompassing a first inner operation opening allowing access through said first frame from a top side of the first frame to a bottom side of the first frame, said first frame elements having a downward first adhesion surface including an adhesive material adapted to adhere said first adhesion surface to the patient's skin;

a first foil, attached to the first frame and extending across said inner operation opening;

a fluid channel provided in said first frame, said fluid channel being in fluid communication with a connector for injecting fluid into said fluid channel, wherein said fluid channel opens into a space between a bottom side of the first frame and the first foil to allow flooding of a space defined between the first foil and the patient's skin if the first frame is attached to said patient's skin;

wherein the first foil comprises a removal extension for removing the first foil, the device further comprising:

a second frame having second frame elements encompassing a second inner operation opening;

a second foil, attached to the second frame and extending across said second inner operation opening;

said second frame having an outer dimension such that the second frame fits into the first frame; and said second frame elements having a downward second adhesion surface including an adhesive material adapted to adhere said second adhesion surface to the patient's skin upon removal of the first foil.

2. The device according to claim 1, wherein said second foil has a bottom surface facing towards a bottom side, wherein said bottom surface is coated with a first adhesive material adapted to attach said second foil to the skin of the patient, and an edge region of said second foil is reinforced or is coated with a second adhesive material having stronger adhesive properties than said first adhesive material.

3. The device according to claim 1, wherein a second fluid channel is provided in said first frame, said second fluid channel being in fluid communication with a second connector for removing fluid out of said second fluid channel, wherein said second fluid channel opens into said space between the bottom side of the first frame and the first foil to allow flooding of said space defined between the first foil and the patient's skin if the first frame is attached to said patient's skin.

4. The device according to claim 3, wherein said first fluid channel opens into said space on a first side of the frame and said second fluid channel opens into said space on a second side of the frame, which is opposite to said first side.

5. The device according to claim 1, wherein said first foil or said second foil is attached to a collapsible frame, wherein said collapsible frame in a first, upright condition defines side walls of a space having a cross section generally corresponding to said first or second inner opening, respectively, and wherein said collapsible frame can be collapsed to a second condition, wherein said collapsible frame is lying flat on said first or second foil, respectively, and protects an edge region of said foil against mechanical impact.

* * * * *